United States Patent
Alving et al.

(10) Patent No.: US 12,411,140 B2
(45) Date of Patent: Sep. 9, 2025

(54) METHODS FOR CHARACTERIZING COMPOSITIONS COMPRISING PEANUT ANTIGENS

(71) Applicant: SANOFI, Paris (FR)

(72) Inventors: Kim Alving, Bridgewater, NJ (US); Pierre deMontigny, Bridgewater, NJ (US); Bing Huang Wang, Bridgewater, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 17/523,050

(22) Filed: Nov. 10, 2021

(65) Prior Publication Data

US 2022/0170942 A1 Jun. 2, 2022

Related U.S. Application Data

(60) Continuation of application No. 16/580,638, filed on Sep. 24, 2019, now Pat. No. 11,199,548, which is a division of application No. 15/392,233, filed on Dec. 28, 2016, now Pat. No. 10,466,250.

(60) Provisional application No. 62/272,094, filed on Dec. 29, 2015.

(51) Int. Cl.
G01N 33/68 (2006.01)

(52) U.S. Cl.
CPC ... *G01N 33/6848* (2013.01); *G01N 2333/415* (2013.01)

(58) Field of Classification Search
CPC ......... G01N 2333/415; G01N 33/6848; G01N 30/72; G01N 30/7233; Y10T 436/24; Y10T 436/25; Y10T 436/25125
USPC ............. 436/20, 86, 89, 161, 173, 174, 175; 435/23
See application file for complete search history.

(56) References Cited

U.S. PATENT DOCUMENTS

| | | | |
|---|---|---|---|
| 10,466,250 B2 * | 11/2019 | Alving | G01N 33/6848 |
| 11,175,271 B2 * | 11/2021 | Seki | G01N 33/02 |
| 11,199,548 B2 * | 12/2021 | Alving | G01N 33/6848 |
| 2011/0229523 A1 * | 9/2011 | Koppelman | A61K 39/36 530/403 |
| 2011/0294700 A1 | 12/2011 | Thelen et al. | |
| 2014/0271721 A1 | 9/2014 | Walser et al. | |
| 2016/0025741 A1 * | 1/2016 | Lock | G01N 33/6848 435/23 |
| 2017/0219600 A1 | 8/2017 | Alving et al. | |
| 2020/0116732 A1 | 4/2020 | Alving et al. | |
| 2022/0326198 A1 * | 10/2022 | Chang | G01N 30/06 |

FOREIGN PATENT DOCUMENTS

| | | |
|---|---|---|
| AU | 200143769 A1 | 8/2001 |
| CN | 1930474 A | 3/2007 |
| CN | 103582652 A | 2/2014 |
| CN | 104569243 A | 4/2015 |
| CN | 104987363 A | 10/2015 |
| EP | 3397970 A2 | 11/2018 |
| WO | WO 2013/033713 A1 | 3/2013 |
| WO | WO 2013/087119 A1 | 6/2013 |
| WO | WO 2017/115139 A2 | 7/2017 |

OTHER PUBLICATIONS

Parker et al. Journal of Agricultural and Food Chemistry, vol. 63, pp. 10669-10680, Nov. 23, 2015.*
Pedreschi et al. Nutrients, vol. 4, pp. 132-150, Feb. 21, 2012.*
Shefcheck et al. Jounral of Agricultural and Food Chemistry, vol. 54, pp. 7953-7959, Sep. 22, 2006.*
Latif et al. Food Chemistry, vol. 136, pp. 213-217, Aug. 8, 2012.*
Flinterman et al. Clinical and Experimental Allergy, vol. 37, pp. 1221-1228, 2007.*
Careri et al. Analytical and Bioanalytical Chemistry, vol. 389, pp. 1901-1907, Sep. 27, 2007.*
Arkwright, et al. (2013) "IgE Sensitization to the Nonspecific Lipid-Transfer Protein Ara H 9 and Peanut-Associated Bronchospasm", BioMed Research International, vol. 2013, Article ID 746507, 9 Pages.
Careri, et al. (Dec. 2007) "Use of Specific Peptide Biomarkers for Quantitative Confirmation of Hidden Allergenic Peanut Proteins Ara H 2 and Ara H 3/4 for Food Control by Liquid Chromatography-Tandem Mass Spectrometry", Analytical and Bioanalytical Chemistry, vol. 389, No. 6, pp. 1901-1907.
Chassaigne, et al. (May 30, 2007) "Proteomics-Based Approach to Detect and Identify Major Allergens in Processed Peanuts by Capillary LC-Q-TOF (MS/MS)", Journal of Agricultural and Food Chemistry, vol. 55, No. 11, pp. 4461-4473.
De Leon, et al. (Jan. 9, 2007) "The Peanut Allergy Epidemic: Allergen Molecular Characterization and Prospects for Specific Therapy", Expert Reviews in Molecular Medicine, vol. 9, No. 1, pp. 1-18.
European Medicines Agency (Nov. 20, 2008) "Committee for Medicinal Products for Human Use (Chmp): Guideline on Allergen Products: Production and Quality Issues", Retrieved from URL: http://www.ema.europa.eu/docs/en_GB/document_library/Scientific_guideline/2009/09/WC500003333, 18 Pages.
Flinterman, et al. (Aug. 2007) "Children with Peanut Allergy Recognize Predominantly Ara H2 And Ara H6, Which Remains Stable Over Time", Clinical and Experimental Allergy, vol. 37, Issue 8, pp. 1221-1228.
Gavage et al. (2020) "High-resolution mass spectrometry-based selection of peanut peptide biomarkers considering food processing and market type variation", Food Chem, vol. 304, 125428.

(Continued)

Primary Examiner — Maureen Wallenhorst
(74) Attorney, Agent, or Firm — LATHROP GPM LLP; James H. Velema, Esq.; Judith L. Stone-Hulslander

(57) ABSTRACT

Methods for determining an in vitro release profile of peanut allergens in a sample are provided. Methods for determining one or more signatures of peanut allergens in a sample are provided.

16 Claims, 2 Drawing Sheets

Specification includes a Sequence Listing.

(56) References Cited

OTHER PUBLICATIONS

Genbank (Aug. 25, 2006) "Arachis hypogaea oleosin 1 mRNA, Complete cds", Accession No. AY722694, National Center for Biotechnology Information, Retrieved From URL: https://www.ncbi.nlm.nih.gov/nuccore/AY722694, 1 Page.
Genbank (Dec. 20, 2006) "Arachis hypogaea Allergen Ara h 2.02 mRNA, Complete cds", Accession No. AY158467, National Center for Biotechnology Information, Retrieved From URL: https://www.ncbi.nlm.nih.gov/nuccore/AY158467, 1 Pages.
Genbank (Feb. 12, 2008) "Arachis hypogaea Ara h 8 Allergen Isoform mRNA, Complete cds", Accession No. EF436550, National Center for Biotechnology Information, Retrieved From URL: https://www.ncbi.nlm.nih.gov/nuccore/EF436550, 1 Page.
Genbank (Feb. 8, 2005) "Arachis hypogaea Ara h 8 Allergen mRNA, Complete cds", Accession No. AY328088, National Center for Biotechnology Information, Retrieved From URL: https://www.ncbi.nlm.nih.gov/nuccore/AY328088, 1 Page.
Genbank (Jul. 25, 2005) "Arachis hypogaea oleosin 1 mRNA, Complete cds", Accession No. DQ097716, National Center for Biotechnology Information, Retrieved From URL: https://www.ncbi.nlm.nih.gov/nuccore/DQ097716.1/, 1 Page.
Genbank (Jul. 25, 2016) "Arachis hypogaea Glycinin (Arah3) mRNA, Partial cds", Accession No. AF093541, National Center for Biotechnology Information, Retrieved From https://www.ncbi.nlm.nih.gov/nuccore/AF093541_, 2 Pages.
Genbank (Jul. 26, 2016) "Arachis hypogaea Allergen Arah6 (Ara h 6) mRNA, Partial cds", Accession No. AF092846, National Center for Biotechnology Information, Retrieved From URL: https://www.ncbi.nlm.nih.gov/nuccore/AF092846, 1 Page.
Genbank (Jul. 26, 2016) "Arachis hypogaea Allergen II Gene, Partial cds", Accession No. AY007229, National Center for Biotechnology Information, Retrieved From URL: https://www.ncbi.nlm.nih.gov/nuccore/AY007229, 1 Page.
Genbank (Jul. 26, 2016) "Arachis hypogaea LTP Isoallergen 2 mRNA, Partial cds", Accession No. EU161278, National Center for Biotechnology Information, Retrieved From URL: https://www.ncbi.nlm.nih.gov/nuccore/EU161278, 1 Page.
Genbank (Jul. 26, 2016) "Arachis hypogaea oleosin 2 mRNA, Partial cds", Genbank Database, Accession No. AY722695, National Center for Biotechnology Information, Retrieved From URL: https://www.ncbi.nlm.nih.gov/nuccore/AY722695, 1 Page.
Genbank (May 18, 2004) "oleosin Isoform [Arachis hypogaea]", Accession No. AAT11925, National Center for Biotechnology Information, Retrieved From URL: https://www.ncbi.nlm.nih.gov/protein/AAT11925, 1 Page.
Genbank (May 24, 1996) "Arachis hypogaea (clone P41b) Ara hl mRNA, Complete cds", Accession No. L34402, National Center for Biotechnology Information, Retrieved From URL: https://www.ncbi.nlm.nih.gov/nuccore/L34402, 2 Pages.
Genbank (Nov. 19, 2007) "1N15 Full Length Peanut Pod cDNA Library Arachis hypogaea cDNA Clone 1 N 15 5—Similar to Defensin, mRNA Sequence", Accession No. EY396019, National Center for Biotechnology information, Retrieved From URL: https://www.ncbi.nlm.nih.gov/nucest/EY396019, 2 Pages.
Genbank (Nov. 19, 2007) "5J9 Full Length Peanut pod cDNA Library Arachis hypogaea cDNA Clone 5J9 5—Similar to Putative Defensin 2.1 Precursor, mRNA Sequence", Accession No. EY396089, National Center for Biotechnology Information, Retrieved From URL: https://www.ncbi.nlm.nih.gov/nucest/EY396089, 2 Pages.
Genbank (Oct. 7, 2009) "Arachis hypogaea LTP Isoallergen 1 Precursor, mRNA, Complete cds", Accession No. EU159429, National Center for Biotechnology Information, Retrieved From URL: https://www.ncbi.nlm.nih.gov/nuccore/EU159429, 1 Page.
Genbank (Oct. 8, 1999) "Arachis hypogaea Allergen (Ara h 7) mRNA, Complete cds", Accession No. AF091737, National Center for Biotechnology Information, Retrieved From URL: https://www.ncbi.nlm.nih.gov/nuccore/AF091737, 1 Page.
Genbank (Oct. 8, 1999) "Arachis hypogaea Profilin (Ara h 5) mRNA, Complete cds", Accession No. AF059616, National Center for Biotechnology Information, Retrieved From URL: https://www.ncbi.Nlm.nih.gov/nuccore/AF059616, 1 Page.
Genbank (Sep. 13, 2005) "oleosin Variant A [Arachis hypogaea]", Accession No. AAK13449, National Center for Biotechnology Information, Retrieved From URL: https://www.ncbi.nlm.nih.gov/protein/AAK13449, 1 Page.
Genbank (Sep. 13, 2005) "oleosin Variant B [Arachis hypogaea]", Accession No. AAK13450, National Center for Biotechnology Information, Retrieved From URL: https://www.ncbi.nlm.nih.gov/protein/AAK13450, 1 Page.
Genbank (Sep. 13, 2010) "Arachis hypogaea Ara h 7 Allergen Precursor, mRNA, Complete cds", Accession No. EU046325, National Center for Biotechnology Information, Retrieved From URL: https://NWW.ncbi.nlm.nih.gov/nuccore/EU046325, 1 Page.
Genbank (Sep. 19, 2004) "oleosin 3 [Arachis hypogaea]", Accession No. AAU21501, National Center for Biotechnology Information, Retrieved From URL: https://www.ncbi.nlm.nih.gov/protein/AAU21501, 1 Page.
Genbank (Sep. 29, 1999) "Arachis hypogaea Glycinin (Arah4) mRNA, Complete cds", Accession No. AF086821, National Center for Biotechnology Information, Retrieved From URL: https://www.ncbi.nlm.nih.gov/nuccore/AF086821, 2 Pages.
International Search Report and Written Opinion received for PCT Patent Application No. PCT/IB2016/01944, mailed on Jul. 7, 2017, 17 Pages.
Koppelman et al. (2010) "Digestion of peanut allergens Ara h 1, Ara h 2, Ara h 3, and Ara h 6: A comparative in vitro study and partial characterization of digestion-resistant peptides", Mol. Nutr. Food Res., 54(12), pp. 1711-1721.
Latif, et al. (Jan. 1, 2013) "Amino Acid Composition, Antinutrients and Allergens in the Peanut Protein Fraction Obtained by an Aqueous Enzymatic Process", Food Chemistry, vol. 136, Issue 1, pp. 213-217.
Martin, et al. (Summer 2011) "Selection of Dissolution Medium for QC Testing of Drug Products", Journal of Validation Technology, pp. 7-11.
Parker, et al. (Dec. 16, 2015) "Multi-Allergen Quantitation and the Impact of Thermal Treatment in Industry-Processed Baked Goods by ELISA and Liquid Chromatography-Tandem Mass Spectrometry", Journal of Agricultural and Food Chemistry, vol. 63, No. 49, pp. 10669-10680.
Pedreschi, et al. (Feb. 2012) "Current Challenges in Detecting Food Allergens by Shotgun and Targeted Proteomic Approaches: A Case Study on Traces of Peanut Allergens in Baked Cookies", Nutrients, vol. 4, No. 2, pp. 132-150.
Picariello, et al. (Mar. 11, 2013) "Proteomic-Based Techniques for the Characterization of Food Allergens", Foodomics: Advanced Mass Spectrometry in Modern Food Science and Nutrition, pp. 69-100.
Powell, et al. (Sep.-Oct. 1998) "Compendium of Excipients for Parenteral Formulations", PDA Journal of Pharmaceutical Science and Technology, vol. 52, No. 5, pp. 238-311.
Ree, Ronald Van. (Jul. 25, 2008) "Allergen Extracts and Standardization", Allergy and Allergic Diseases, pp. 928-941.
Sealey-Voyksner, et al. (Jul. 14, 2015) "Discovery of Highly Conserved Unique 14-16. Peanut and Tree Nut Peptides By LC-MS/MS 19-22 for Multi-Allergen Detection", Food chemistry, vol. 194, pp. 201-211.
Seppala, et al. (Apr. 1, 2011) "Absolute Quantification of Allergens from Complex Mixtures: A New Sensitive Tool for Standardization of Allergen Extracts for Specific Immunotherapy", Journal of Proteome Research, vol. 10, No. 4, pp. 2113-2122.
Shefcheck, et al. (2006) "Confirmation of Peanut Protein Using Peptide Markers in Dark Chocolate Using Liquid Chromatography-Tandem Mass Spectrometry (LC-MS/MS)", Journal of Agricultural and Food Chemistry, vol. 54, No. 21, pp. 7953-7959.
UniProt (Apr. 13, 2016) "UniProtKB—B3EWP3 (DEF1_ARAHY)", Accession No. B3EWP3, UniProt Consortium, Retrieved From URL: http://www.uniprot.org/uniprot/B3EWP3, 5 Pages.

(56) References Cited

OTHER PUBLICATIONS

UniProt (Apr. 13, 2016) "UniProtKB—B3EWP4 (DEF2_ARAHY)", Accession No. B3EWP4, UniProt Consortium, Retrieved From URL: http://www.uniprot.org/uniprot/B3EWP4, 5 Pages.
UniProt (Apr. 29, 2008) "UniProtKB—B1PYZ4 (B1PYZ4_ARAHY)", Accession No. B1PYZ4, UniProt Consortium, Retrieved From URL: http://lwww.uniprot.org/uniprot/B1PYZ4, 4 Pages.
UniProt (Apr. 3, 2013) "UniProtKB—L70H52 (L70H52_ARAHY)", Accession No. L70H52, UniProt Consortium, Retrieved From URL: http://www.uniprot.org/uniprot/L70H52, 4 Pages.
UniProt (Apr. 8, 2008) "UniProtKB—B0YIU5 (B0YIU5_ARAHY)", Accession No. B0YIU5, UniProt Consortium, Retrieved From URL: http://www.uniprot.org/uniprot/B0YIU5, 4 Pages.
UniProt (Dec. 1, 2001) "UniProtKB—Q43375 (Q43375_ARAHY)", Accession No. 043375, UniProt Consortium, Retrieved From URL: http://www.uniprot.org/uniprot/Q43375, 4 Pages.
UniProt (Dec. 20, 2005) "UniProtKB—Q2YHR1 (Q2YHR1_ARAHY)", Accession No. Q2YHR1, UniProt Consortium, Retrieved From URL: http://www.uniprot.org/uniprot/Q2YHR1, 4 Pages.
UniProt (Feb. 15, 2005) "UniProtKB—Q516T2 (Q516T2_ARAHY)", Accession No. 0516T2, UniProt Consortium, Retrieved From URL: http://www.uniprot.org/uniprot/Q516T2, 5 Pages.
UniProt (Feb. 8, 2011) "UniProtKB—E5G076 (E5G076_ARAHY)", Accession No. E5G076, UniProt Consortium, Retrieved From URL: http://www.uniprot.org/uniprot/E5G076, 4 Pages.
UniProt (Feb. 8, 2011) "UniProtKB—E5G077 (E5G077 ARAHY)", Accession No. E5G077, UniProt Consortium, Retrieved From URL: http://www.uniprot.org/uniprot/E5G077, 5 Pages.
UniProt (Jan. 15, 2008) "UniProtKB—A8VT41 (A8VT41_ARADU)", Accession No. A8VT41, UniProt Consortium, Retrieved From URL: http:/lwww.uniprot.org/uniprot/A8VT41, 4 Pages.
UniProt (Jan. 15, 2008) "UniProtKB—A8VT44 (A8VT44_ARADU)", Accession No. A8VT44, UniProt Consortium, Retrieved From URL: http:/lwww.uniprot.org/uniprot/A8VT44, 4 Pages.
UniProt (Jan. 15, 2008) "UniProtKB—A8VT45 (A8VT45_ARADU)", Accession No. A8VT45, UniProt Consortium, Retrieved From URL: http:/lwww.uniprot.org/uniprot/A8VT45, 4 Pages.
UniProt (Jan. 15, 2008) "UniProtKB—A8VT50 (A8VT50_ARADU)", Accession No. A8VT50, UniProt Consortium, Retrieved From URL: http:/lwww.uniprot.org/uniprot/A8VT50, 4 Pages.
UniProt (Jan. 23, 2007) "Uniport—A1DZE9 (A1DZE9_ARAHY)", Accession No. A1DZE9., UniProt Consortium, Retrieved From URL: http://www.uniprot.org/uniprot/A1DZE9, 4 Pages.
UniProt (Jan. 23, 2007) "UniProtKB—A1DZF0 (A1DZF0_ARAHY)", Accession No. A1DZF0, UniProt Consortium, Retrieved From URL: http://www.uniprot.org/uniprot/A1DZF0, 5 Pages.
UniProt (Jan. 23, 2007) "UniProtKB—A1DZF1 (A1DZF1_ARAHY)", Accession No. A1DZF1, UniProt Consortium, Retrieved From URL: http://www.uniprot.org/uniprot/A1DZF1, 4 Pages.
UniProt (Jul. 5, 2004) "UniProtKB—Q6IWG5 (Q6IWG5_ARAHY)", Accession No. Q6IWG5, UniProt Consortium, Retrieved From URL: http://www.uniprot.org/uniprot/Q6IWG5, 5 Pages.
UniProt (Jul. 5, 2004) "UniProtKB—Q6PSU3 (Q6PSU3_ARAHY)", Accession No. Q6PSU3, UniProt Consortium, Retrieved From URL: http://www.uniprot.org/uniprot/Q6PSU3, 4 Pages.
UniProt (Jul. 5, 2004) "UniProtKB—Q6J1J8 (Q6J1J8_ARAHY)", Accession No. Q6J1J8, UniProt Consortium, Retrieved From URL: http://www.uniprot.org/uniprot/Q6J1J8, 4 Pages.
UniProt (Jul. 5, 2004) "UniProtKB—Q6PSU4 (Q6PSU4_ARAHY)", Accession No. Q6PSU4, UniProt Consortium, Retrieved From URL: http://www.uniprot.org/uniprot/Q6PSU4, 4 Pages.
UniProt (Jul. 1, 2008) "UniProtKB—B2ZGS2 (B2ZGS2_ARAHY)", Accession No. B2ZGS2, UniProt Consortium, Retrieved From URL: http:/lwww.uniprot.org/uniprot/B2ZGS2, 4 Pages.
UniProt (Jul. 10, 2007) "UniProtKB—A5Z1Q5 (A5Z1Q5_ARADU)", Accession No. A5Z1Q5, UniProt Consortium, Retrieved From URL: http://www.uniprot.org/uniprot/A5Z1Q5, 4 Pages.
UniProt (Jul. 10, 2007) "UniProtKB—A5Z1Q6 (A5Z1Q6_ARAIP)", Accession No. A5Z1Q6, UniProt Consortium, Retrieved From URL: http://www.uniprot.org/uniprot/A5Z1Q6, 4 Pages.
UniProt (Jul. 10, 2007) "UniProtKB—A5Z1Q8 (A5Z1Q8_ARADU)", Accession No. A5Z1Q8, UniProt Consortium, Retrieved From URL: http://www.uniprot.org/uniprot/A5Z1Q8, 4 Pages.
UniProt (Jul. 10, 2007) "UniProtKB—A5Z1Q9 (A5Z1Q9_ARAIP)", Accession No. A5Z1Q9, UniProt Consortium, Retrieved From URL: http://www.uniprot.org/uniprot/A5Z1Q9, 4 Pages.
UniProt (Jul. 10, 2007) "UniProtKB—A5Z1R0 (A5Z1R0_ARAHY)", Accession No. A5Z1R0, UniProt Consortium, Retrieved From URL: http://www.uniprot.org/uniprot/A5Z1 RD, 4 Pages.
UniProt (Jul. 5, 2004) "UniProtKB—Q6PSU5 (Q6PSU5_ARAHY)", Accession No. Q6PSU5, UniProt Consortium, Retrieved From URL: http://www.uniprot.org/uniprot/Q6PSU5, 4 Pages.
UniProt (Jul. 5, 2004) "UniProtKB—Q6PSU6 (Q6PSU6_ARAHY)", Accession No. Q6PSU6, UniProt Consortium, Retrieved From URL: http://www.uniprot.org/uniprot/Q6PSU6, 4 Pages.
UniProt (Jul. 5, 2004) "UniProtKB—Q6T2T4 (Q6T2T4_ARAHY)", Accession No. Q6T2T4, UniProt Consortium, Retrieved From URL : http://www.uniprot.org/uniprot/Q6T2T4, 5 Pages.
UniProt (Jul. 5, 2004) "UniProtKB—Q6VT83 (Q6VT83_ARAHY)", Accession No. Q6VT83, UniProt Consortium, Retrieved From URL: http://www.uniprot.org/uniprot/Q6VT83, 4 Pages.
UniProt (Jun. 1, 2001) "UniProtKB—Q9AXI0 (Q9AXI0_ARAHY)", Accession No. Q9AXI0, UniProt Consortium, Retrieved From URL: http://www.uniprot.org/uniprot/Q9AXI0, 3 Pages.
UniProt (Jun. 1, 2001) "UniProtKB—Q9AXI1 (Q9AXI1_ARAHY)", Accession No. Q9AXI1, UniProt Consortium, Retrieved From URL: http://www.uniprot.org/uniprot/Q9AXI1, 3 Pages.
UniProt (Jun. 26, 2013) "UniProtKB—N1NEW2 (N1NEW2_ARADU)", Accession No. N1NEW2, UniProt Consortium, Retrieved From URL: http://www.uniprot.org/uniprot/N1 NEW2, 4 Pages.
UniProt (Jun. 26, 2013) "UniProtKB—N1NG13 (N1NG13_ARAHY)", Accession No. N1NG13, UniProt Consortium, Retrieved From URL: http://www.uniprot.org/uniprot/N1 NG13, 4 Pages.
UniProt (Mar. 1, 2001) "UniProtKB—Q9FZ11 (Q9FZ11_ARAHY)", Accession No. Q9FZ11, UniProt Consortium, Retrieved From URL: http://www.uniprot.org/uniprot/Q9FZ11, 5 Pages.
UniProt (Mar. 1, 2002) "UniProtKB—Q8W0P8 (Q8W0P8_ARAHY)", Accession No. Q8W0P8, UniProt Consortium, Retrieved From URL: http://www.uniprot.org/uniprot/Q8W0P8, 4 Pages.
UniProt (Mar. 23, 2010) "UniProtKB—D3K177 (D3K177_ARAHY)", Accession No. D3K177, UniProt Consortium, Retrieved From URL: http://www.uniprot.org/uniprot/D3K177, 5 Pages.
UniProt (May 1, 2000) "UniProtKB—Q9SQH1 (Q9SQH1_ARAHY)", Accession No. Q9SQH1, UniProt Consortium, Retrieved From URL: http://www.uniprot.org/uniprot/Q9SQH1, 4 Pages.
UniProt (May 1, 2000) "UniProtKB—Q9SQH7 (Q9SQH7_ARAHY)", Accession No. Q9SQH7, UniProt Consortium, Retrieved From URL: http://www.uniprot.org/uniprot/Q9SQH7, 5 Pages.
UniProt (May 1, 2000) "UniProtKB—Q9SQI9 (PROF_ARAHY)", Accession No. Q9SQI9, UniProt Consortium, Retrieved From URL: http://www.uniprot.org/uniprot/Q9SQI9, 5 Pages.
UniProt (May 15, 2007) "UniProtKB—Q6PSU2 (CONG7_ARAHY)", Accession No. Q6PSU2, UniProt Consortium, Retrieved From URL: http://www.uniprot.org/uniprot/Q6PSU2, 8 Pages.
UniProt (Nov. 1, 1995) "UniProtKB—P43237 (ALL 11_ARAHY)", Accession No. P43237, UniProt Consortium, Retrieved From URL: http://www.uniprot.org/uniprot/P43237, 5 p.
UniProt (Nov. 1, 1995) "UniProtKB—P43238 (ALL 12_ARAHY)", Accession No. P43238, UniProt Consortium, Retrieved From URL: http://www.uniprot.org/uniprot/P43238, 6 p.
UniProt (Nov. 1, 1996) "UniProtKB—Q38711 (Q38711_ARAHY)", Accession No. Q38711, UniProt Consortium, Retrieved From URL: http://www.uniprot.org/uniprot/Q38711, 4 Pages.
UniProt (Nov. 1, 1996) "UniProtKB—Q43373 (Q43373_ARAHY)", Accession No. Q43373, UniProt Consortium, Retrieved From URL: http://www.uniprot.org/uniprot/Q43373, 4 Pages.
UniProt (Nov. 1, 1998) "UniProtKB—O82580 (O82580_ARAHY)", Accession No. O82580, UniProt Consortium, Retrieved From URL: http://www.uniprot.org/uniprot/082580, 4 Pages.
UniProt (Nov. 25, 2008) "UniProtKB—B6CEX8 (B6CEX8_ARAHY)", Accession No. B6CEX8, UniProt Consortium, Retrieved From URL: http://www.uniprot.org/uniprot/B6CEX8, 4 Pages.

(56) References Cited

OTHER PUBLICATIONS

UniProt (Nov. 25, 2008) "UniProtKB—B6CG41 (B6CG41_ARAHY)", Accession No. B6CG41, UniProt Consortium, Retrieved From URL: http://www.uniprot.org/uniprot/B6CG41, 4 Pages.
UniProt (Nov. 4, 2008) "UniProtKB—B5TYU1 (B5TYU1_ARAHY)", Accession No. B5TYU1, UniProt Consortium, Retrieved From URL: http://www.uniprot.org/uniprot/B5TYU1, 5 Pages.
UniProt (Oct. 1, 1996) "UniProtKB—P02872 (LECG_ARAHY)", Accession No. P02872, UniProt Consortium, Retrieved From URL: http://www.uniprot.org/uniprot/P02872, 7 p.
UniProt (Oct. 1, 2002) "UniProtKB—Q8LKN1 (Q8LKN1_ARAHY)", Accession No. Q8LKN1, UniProt Consortium, Retrieved From URL: http://www.uniprot.org/uniprot/Q8LKN1, 5 Pages.
UniProt (Oct. 1, 2002) "UniProtKB—Q8LL03 (Q8LL03_ARAHY)", Accession No. Q8LL03, UniProt Consortium, Retrieved From URL: http://www.uniprot.org/uniprot/Q8LL03, 4 Pages.
UniProt (Oct. 25, 2004) "UniProtKB—Q647G3 (Q647G3_ARAHY)", Accession No. Q647G3, UniProt Consortium, Retrieved From URL: http://www.uniprot.org/uniprot/Q647G3, 4 Pages.
UniProt (Oct. 25, 2004) "UniProtKB—Q647G4 (Q647G4_ARAHY)", Accession No. Q647G4, UniProt Consortium, Retrieved From URL: http://www.uniprot.org/uniprot/Q647G4, 3 Pages.
UniProt (Oct. 25, 2004) "UniProtKB—Q647G8 (Q647G8_ARAHY)", Accession No. Q647G8, UniProt Consortium, Retrieved From URL: http://www.uniprot.org/uniprot/Q647G8, 4 Pages.
UniProt (Oct. 25, 2004) "UniProtKB—Q647G9 (CONG_ARAHY)", Accession No. Q647G9, UniProt Consortium, Retrieved From URL: http://www.uniprot.org/uniprot/Q647G9, 6 Pages.
UniProt (Oct. 25, 2004) "UniProtKB—Q647H2 (AHY3_ARAHY)", Accession No. Q647H2, UniProt Consortium, Retrieved From URL: http://www.uniprot.org/uniprot/Q647H2, 5 Pages.
UniProt (Oct. 25, 2004) "UniProtKB—Q647H3 (Q647H3_ARAHY)", Accession No. Q647H3, UniProt Consortium, Retrieved From URL: http://www.uniprot.org/uniprot/Q647H3, 5 Pages.
UniProt (Oct. 25, 2004) "UniProtKB—Q647H4 (Q647H4_ARAHY)", Accession No. Q647H4, UniProt Consortium, Retrieved From URL: http://www.uniprot.org/uniprot/Q647H4, 5 Pages.
UniProt (Oct. 3, 2006) "UniProtKB—Q0GM57 (Q0GM57_ARAHY)", Accession No. Q0GM57, UniProt Consortium, Retrieved From URL: http://www.uniprot.org/uniprot/Q0GM57, 5 Pages.
UniProt (Oct. 3, 2006) "UniProtKB—Q647G5 (Q647G5_ARAHY)", Accession No. Q647G5, UniProt Consortium, Retrieved From URL: http://www.uniprot.org/uniprot/Q647G5, 3 Pages.
UniProt (Sep. 13, 2005) "UniProtKB—Q45W87 (Q45W87_ARAHY)", Accession No. Q45W87, UniProt Consortium, Retrieved From URL: http://www.uniprot.org/uniprot/Q45W87, 3 Pages.
UniProt (Sep. 13, 2005)) "UniProtKB—Q45W86 (Q45W86_ARAHY)", Accession No. Q45W86, UniProt Consortium, Retrieved From URL: http://www.uniprot.org/uniprot/Q45W86, 3 Pages.
UniProt (Sep. 2, 2008) "UniProtKB—B31XL2 (B31XL2_ARAHY)", Accession No. B31XL2, UniProt Consortium, Retrieved From URL: http://www.uniprot.org/uniprot/B31XL2, 4 Pages.
UniProt (Sep. 23, 2008) "UniProtKB—B4XID4 (B4XID4_ARAHY)", Accession No. B4XID4, UniProt Consortium, Retrieved From URL: http://www.uniprot.org/uniprot/B4XID4, 4 Pages.
UniProt (Sep. 5, 2006) "UniProtKB—Q0PKR4 (Q0PKR4_ARAHY)", Accession No. Q0PKR4, UniProt Consortium, Retrieved From URL: http://www.uniprot.org/uniprot/Q0PKR4, 4 Pages.
UniProt, (Nov. 23, 2004) "UniProtKB—Q5XXQ5 (Q5XXQ5_ARAHY)", Accession No. Q5XXQ5, UniProt Consortium, Retrieved From URL: http://www.uniprot.org/uniprot/Q5XXQ5, 4 Pages.
U.S. Appl. No. 15/392,233 2017/0219600 U.S. Pat. No. 10,466,250, filed Dec. 28, 2016 Aug. 3, 2017 Nov. 5, 2019, Kim Alving, Methods for Characterizing Compositions Comprising Peanut Antigens
U.S. Appl. No. 16/580,638 2020/0116732 U.S. Pat. No. 11,199,548, filed Sep. 24, 2019 Apr. 16, 2020 Dec. 14, 2021, Kim Alving, Methods for Characterizing Compositions Comprising Peanut Antigens.
U.S. Appl. No. 17/523,050 2022/0170942, filed Nov. 10, 2021 Jun. 2, 2022, Kim Alving, Methods for Characterizing Compositions Comprising Peanut Antigens.
Extended European Search Report for European Patent Application No. 23167597.6, dated Oct. 13, 2023.
Koeberl et al., "Next Generation of Food Allergen Quantification Using Mass Spectrometric Systems", Journal of Proteome Research, Aug. 2014, 13(8): 3499-3509.
Kottapalli et al., "Proteomics analysis of mature seed of four peanut cultivars using two-dimensionalgel electrophoresis reveals distinct differential expression of storage, anti-nutritional, and allergenic proteins", Plant Science, May 15, 2008, 175: 321-329.
Monaci et al., "High-resolution Orbitrap(TM)-based mass spectrometry for rapid detection of peanuts in nuts", Food Additives & Contaminants: Part A, Jul. 29, 2015, 32(10): 1607-1616.

\* cited by examiner

| Sequence | missed | FDR | PTM | BLAST | Database | presence in isoforms |
|---|---|---|---|---|---|---|
| GTGNLELVAVR | 0 | <1% | none | OK | Peanut | present in 7 protein isoforms of Ara H1 |

Figure 1A

| #1 | $b^+$ | $b^{2+}$ | Seq. | $y^+$ | $y^{2+}$ | #2 |
|---|---|---|---|---|---|---|
| 1 | 58.02875 | 29.51801 | G | | | 11 |
| 2 | 159.07643 | 80.04185 | T | 1071.62 | 536.312 | 10 |
| 3 | 216.0979 | 108.55259 | G | 970.568 | 485.788 | 9 |
| 4 | 330.14083 | 165.57405 | N | 913.547 | 457.277 | 8 |
| 5 | 443.2249 | 222.11609 | L | 799.504 | 400.255 | 7 |
| 6 | 572.2675 | 286.63739 | E | 686.42 | 343.713 | 6 |
| 7 | 685.35157 | 343.17942 | L | 557.377 | 279.192 | 5 |
| 8 | 784.41999 | 392.71363 | V | 444.293 | 222.65 | 4 |
| 9 | 855.45711 | 428.23219 | A | 345.225 | 173.116 | 3 |
| 10 | 954.52553 | 477.7664 | V | 274.187 | 137.597 | 2 |
| 11 | | | R | 175.119 | 88.0631 | 1 |

Figure 1B

SEQUENCE LISTING

<160> NUMBER OF SEQ ID NOS: 253

<210> SEQ ID NO 1
<211> LENGTH: 14
<212> TYPE: PRT
<213> ORGANISM: Arachis hypogaea

<400> SEQUENCE: 1

```
Ala Cys Glu Ser Arg Cys Thr Lys Leu Glu Tyr Asp Pro Arg
1               5                   10

<210> SEQ ID NO 2
<211> LENGTH: 20
<212> TYPE: PRT
<213> ORGANISM: Arachis hypogaea

<400> SEQUENCE: 2

Ala Cys Glu Ser Arg Cys Thr Lys Leu Glu Tyr Asp Pro Arg Cys Val
1               5                   10                  15

Tyr Asp Pro Arg
            20

<210> SEQ ID NO 3
<211> LENGTH: 9
<212> TYPE: PRT
<213> ORGANISM: Arachis hypogaea

<400> SEQUENCE: 3

Ala Met Val Ile Val Val Val Asn Lys
1               5

<210> SEQ ID NO 4
<211> LENGTH: 20
<212> TYPE: PRT
<213> ORGANISM: Arachis hypogaea

<400> SEQUENCE: 4

Ala Met Val Ile Val Val Val Asn Lys Gly Thr Gly Asn Leu Glu Leu
1               5                   10                  15

Val Ala Val Arg
            20

<210> SEQ ID NO 5
<211> LENGTH: 21
<212> TYPE: PRT
<213> ORGANISM: Arachis hypogaea

<400> SEQUENCE: 5

Ala Met Val Ile Val Val Val Asn Lys Gly Thr Gly Asn Leu Glu Leu
1               5                   10                  15

Val Ala Val Arg Lys
            20

<210> SEQ ID NO 6
<211> LENGTH: 13
<212> TYPE: PRT
<213> ORGANISM: Arachis hypogaea

<400> SEQUENCE: 6

Cys Leu Gln Ser Cys Gln Gln Glu Pro Asp Asp Leu Lys
1               5                   10

<210> SEQ ID NO 7
<211> LENGTH: 15
<212> TYPE: PRT
<213> ORGANISM: Arachis hypogaea

<400> SEQUENCE: 7

Cys Leu Gln Ser Cys Gln Gln Glu Pro Asp Asp Leu Lys Gln Lys
1               5                   10                  15
```

```
<210> SEQ ID NO 8
<211> LENGTH: 20
<212> TYPE: PRT
<213> ORGANISM: Arachis hypogaea

<400> SEQUENCE: 8

Cys Leu Gln Ser Cys Gln Gln Glu Pro Asp Asp Leu Lys Gln Lys Ala
1               5                   10                  15

Cys Glu Ser Arg
            20

<210> SEQ ID NO 9
<211> LENGTH: 23
<212> TYPE: PRT
<213> ORGANISM: Arachis hypogaea

<400> SEQUENCE: 9

Cys Leu Gln Ser Cys Gln Gln Glu Pro Asp Asp Leu Lys Gln Lys Ala
1               5                   10                  15

Cys Glu Ser Arg Cys Thr Lys
            20

<210> SEQ ID NO 10
<211> LENGTH: 9
<212> TYPE: PRT
<213> ORGANISM: Arachis hypogaea

<400> SEQUENCE: 10

Cys Thr Lys Leu Glu Tyr Asp Pro Arg
1               5

<210> SEQ ID NO 11
<211> LENGTH: 15
<212> TYPE: PRT
<213> ORGANISM: Arachis hypogaea

<400> SEQUENCE: 11

Cys Thr Lys Leu Glu Tyr Asp Pro Arg Cys Val Tyr Asp Pro Arg
1               5                   10                  15

<210> SEQ ID NO 12
<211> LENGTH: 24
<212> TYPE: PRT
<213> ORGANISM: Arachis hypogaea

<400> SEQUENCE: 12

Cys Thr Lys Leu Glu Tyr Asp Pro Arg Cys Val Tyr Asp Pro Arg Gly
1               5                   10                  15

His Thr Gly Thr Thr Asn Gln Arg
            20

<210> SEQ ID NO 13
<211> LENGTH: 6
<212> TYPE: PRT
<213> ORGANISM: Arachis hypogaea

<400> SEQUENCE: 13

Cys Val Tyr Asp Pro Arg
1               5

<210> SEQ ID NO 14
<211> LENGTH: 15
<212> TYPE: PRT
```

```
<213> ORGANISM: Arachis hypogaea

<400> SEQUENCE: 14

Cys Val Tyr Asp Pro Arg Gly His Thr Gly Thr Thr Asn Gln Arg
1               5                   10                  15

<210> SEQ ID NO 15
<211> LENGTH: 21
<212> TYPE: PRT
<213> ORGANISM: Arachis hypogaea

<400> SEQUENCE: 15

Cys Val Tyr Asp Pro Arg Gly His Thr Gly Thr Thr Asn Gln Arg Ser
1               5                   10                  15

Pro Pro Gly Glu Arg
            20

<210> SEQ ID NO 16
<211> LENGTH: 23
<212> TYPE: PRT
<213> ORGANISM: Arachis hypogaea

<400> SEQUENCE: 16

Cys Val Tyr Asp Pro Arg Gly His Thr Gly Thr Thr Asn Gln Arg Ser
1               5                   10                  15

Pro Pro Gly Glu Arg Thr Arg
            20

<210> SEQ ID NO 17
<211> LENGTH: 13
<212> TYPE: PRT
<213> ORGANISM: Arachis hypogaea

<400> SEQUENCE: 17

Asp Leu Ala Phe Pro Gly Ser Gly Glu Gln Val Glu Lys
1               5                   10

<210> SEQ ID NO 18
<211> LENGTH: 16
<212> TYPE: PRT
<213> ORGANISM: Arachis hypogaea

<400> SEQUENCE: 18

Asp Leu Ala Phe Pro Gly Ser Gly Glu Gln Val Glu Lys Leu Ile Lys
1               5                   10                  15

<210> SEQ ID NO 19
<211> LENGTH: 12
<212> TYPE: PRT
<213> ORGANISM: Arachis hypogaea

<400> SEQUENCE: 19

Asp Asn Val Ile Asp Gln Ile Glu Lys Gln Ala Lys
1               5                   10

<210> SEQ ID NO 20
<211> LENGTH: 11
<212> TYPE: PRT
<213> ORGANISM: Arachis hypogaea

<400> SEQUENCE: 20

Asp Gln Ser Ser Tyr Leu Gln Gly Phe Ser Arg
1               5                   10
```

<210> SEQ ID NO 21
<211> LENGTH: 27
<212> TYPE: PRT
<213> ORGANISM: Arachis hypogaea

<400> SEQUENCE: 21

Asp Gln Ser Ser Tyr Leu Gln Gly Phe Ser Arg Asn Thr Leu Glu Ala
1               5                   10                  15

Ala Phe Asn Ala Glu Phe Asn Glu Ile Arg Arg
            20                  25

<210> SEQ ID NO 22
<211> LENGTH: 19
<212> TYPE: PRT
<213> ORGANISM: Arachis hypogaea

<400> SEQUENCE: 22

Glu Asp Gln Glu Glu Glu Asn Gln Gly Gly Lys Gly Pro Leu Leu Ser
1               5                   10                  15

Ile Leu Lys

<210> SEQ ID NO 23
<211> LENGTH: 12
<212> TYPE: PRT
<213> ORGANISM: Arachis hypogaea

<400> SEQUENCE: 23

Glu Asp Trp Arg Arg Pro Ser His Gln Gln Pro Arg
1               5                   10

<210> SEQ ID NO 24
<211> LENGTH: 12
<212> TYPE: PRT
<213> ORGANISM: Arachis hypogaea

<400> SEQUENCE: 24

Glu Glu Asp Trp Arg Gln Pro Arg Glu Asp Trp Arg
1               5                   10

<210> SEQ ID NO 25
<211> LENGTH: 20
<212> TYPE: PRT
<213> ORGANISM: Arachis hypogaea

<400> SEQUENCE: 25

Glu Glu Asp Trp Arg Gln Pro Arg Glu Asp Trp Arg Arg Pro Ser His
1               5                   10                  15

Gln Gln Pro Arg
            20

<210> SEQ ID NO 26
<211> LENGTH: 23
<212> TYPE: PRT
<213> ORGANISM: Arachis hypogaea

<400> SEQUENCE: 26

Glu Glu Glu Glu Asp Glu Asp Glu Glu Glu Gly Ser Asn Arg Glu
1               5                   10                  15

Val Arg Arg Tyr Thr Ala Arg
            20

<210> SEQ ID NO 27

```
<211> LENGTH: 12
<212> TYPE: PRT
<213> ORGANISM: Arachis hypogaea

<400> SEQUENCE: 27

Glu Glu Gly Gly Arg Trp Gly Pro Ala Gly Pro Arg
1               5                   10

<210> SEQ ID NO 28
<211> LENGTH: 14
<212> TYPE: PRT
<213> ORGANISM: Arachis hypogaea

<400> SEQUENCE: 28

Glu Glu Gly Gly Arg Trp Gly Pro Ala Gly Pro Arg Glu Arg
1               5                   10

<210> SEQ ID NO 29
<211> LENGTH: 16
<212> TYPE: PRT
<213> ORGANISM: Arachis hypogaea

<400> SEQUENCE: 29

Glu Glu Gly Gly Arg Trp Gly Pro Ala Gly Pro Arg Glu Arg Glu Arg
1               5                   10                  15

<210> SEQ ID NO 30
<211> LENGTH: 14
<212> TYPE: PRT
<213> ORGANISM: Arachis hypogaea

<400> SEQUENCE: 30

Glu Glu Thr Ser Arg Asn Asn Pro Phe Tyr Phe Pro Ser Arg
1               5                   10

<210> SEQ ID NO 31
<211> LENGTH: 15
<212> TYPE: PRT
<213> ORGANISM: Arachis hypogaea

<400> SEQUENCE: 31

Glu Glu Thr Ser Arg Asn Asn Pro Phe Tyr Phe Pro Ser Arg Arg
1               5                   10                  15

<210> SEQ ID NO 32
<211> LENGTH: 19
<212> TYPE: PRT
<213> ORGANISM: Arachis hypogaea

<400> SEQUENCE: 32

Glu Glu Thr Ser Arg Asn Asn Pro Phe Tyr Phe Pro Ser Arg Arg Phe
1               5                   10                  15

Ser Thr Arg

<210> SEQ ID NO 33
<211> LENGTH: 12
<212> TYPE: PRT
<213> ORGANISM: Arachis hypogaea

<400> SEQUENCE: 33

Glu Gly Ala Leu Met Leu Pro His Phe Asn Ser Lys
1               5                   10

<210> SEQ ID NO 34
```

```
<211> LENGTH: 21
<212> TYPE: PRT
<213> ORGANISM: Arachis hypogaea

<400> SEQUENCE: 34

Glu Gly Ala Leu Met Leu Pro His Phe Asn Ser Lys Ala Met Val Ile
1               5                   10                  15

Val Val Val Asn Lys
            20

<210> SEQ ID NO 35
<211> LENGTH: 42
<212> TYPE: PRT
<213> ORGANISM: Arachis hypogaea

<400> SEQUENCE: 35

Glu Gly Asp Val Phe Ile Met Pro Ala Ala His Pro Val Ala Ile Asn
1               5                   10                  15

Ala Ser Ser Glu Leu His Leu Leu Gly Phe Gly Ile Asn Ala Glu Asn
            20                  25                  30

Asn His Arg Ile Phe Leu Ala Gly Asp Lys
        35                  40

<210> SEQ ID NO 36
<211> LENGTH: 51
<212> TYPE: PRT
<213> ORGANISM: Arachis hypogaea

<400> SEQUENCE: 36

Glu Gly Asp Val Phe Ile Met Pro Ala Ala His Pro Val Ala Ile Asn
1               5                   10                  15

Ala Ser Ser Glu Leu His Leu Leu Gly Phe Gly Ile Asn Ala Glu Asn
            20                  25                  30

Asn His Arg Ile Phe Leu Ala Gly Asp Lys Asp Asn Val Ile Asp Gln
        35                  40                  45

Ile Glu Lys
    50

<210> SEQ ID NO 37
<211> LENGTH: 12
<212> TYPE: PRT
<213> ORGANISM: Arachis hypogaea

<400> SEQUENCE: 37

Glu Gly Glu Pro Asp Leu Ser Asn Asn Phe Gly Lys
1               5                   10

<210> SEQ ID NO 38
<211> LENGTH: 21
<212> TYPE: PRT
<213> ORGANISM: Arachis hypogaea

<400> SEQUENCE: 38

Glu Gly Glu Pro Asp Leu Ser Asn Asn Phe Gly Lys Leu Phe Glu Val
1               5                   10                  15

Lys Pro Asp Lys Lys
            20

<210> SEQ ID NO 39
<211> LENGTH: 38
<212> TYPE: PRT
<213> ORGANISM: Arachis hypogaea
```

<400> SEQUENCE: 39

Glu Gly Glu Pro Asp Leu Ser Asn Asn Phe Gly Lys Leu Phe Glu Val
1               5                   10                  15

Lys Pro Asp Lys Lys Asn Pro Gln Leu Gln Asp Leu Asp Met Met Leu
            20                  25                  30

Thr Cys Val Glu Ile Lys
            35

<210> SEQ ID NO 40
<211> LENGTH: 14
<212> TYPE: PRT
<213> ORGANISM: Arachis hypogaea

<400> SEQUENCE: 40

Glu Gly Glu Gln Glu Trp Gly Thr Pro Gly Ser His Val Arg
1               5                   10

<210> SEQ ID NO 41
<211> LENGTH: 29
<212> TYPE: PRT
<213> ORGANISM: Arachis hypogaea

<400> SEQUENCE: 41

Glu Gly Glu Gln Glu Trp Gly Thr Pro Gly Ser His Val Arg Glu Glu
1               5                   10                  15

Thr Ser Arg Asn Asn Pro Phe Tyr Phe Pro Ser Arg Arg
            20                  25

<210> SEQ ID NO 42
<211> LENGTH: 8
<212> TYPE: PRT
<213> ORGANISM: Arachis hypogaea

<400> SEQUENCE: 42

Glu His Val Glu Glu Leu Thr Lys
1               5

<210> SEQ ID NO 43
<211> LENGTH: 11
<212> TYPE: PRT
<213> ORGANISM: Arachis hypogaea

<400> SEQUENCE: 43

Glu His Val Glu Glu Leu Thr Lys His Ala Lys
1               5                   10

<210> SEQ ID NO 44
<211> LENGTH: 8
<212> TYPE: PRT
<213> ORGANISM: Arachis hypogaea

<400> SEQUENCE: 44

Glu Gln Gln Gln Arg Gly Arg Arg
1               5

<210> SEQ ID NO 45
<211> LENGTH: 23
<212> TYPE: PRT
<213> ORGANISM: Arachis hypogaea

<400> SEQUENCE: 45

Glu Gln Gln Gln Arg Gly Arg Arg Glu Glu Glu Glu Asp Glu Asp Glu

```
1               5                   10                  15
Glu Glu Glu Gly Ser Asn Arg
            20

<210> SEQ ID NO 46
<211> LENGTH: 7
<212> TYPE: PRT
<213> ORGANISM: Arachis hypogaea

<400> SEQUENCE: 46

Glu Arg Glu Glu Asp Trp Arg
1               5

<210> SEQ ID NO 47
<211> LENGTH: 10
<212> TYPE: PRT
<213> ORGANISM: Arachis hypogaea

<400> SEQUENCE: 47

Glu Arg Glu Glu Asp Trp Arg Gln Pro Arg
1               5                   10

<210> SEQ ID NO 48
<211> LENGTH: 9
<212> TYPE: PRT
<213> ORGANISM: Arachis hypogaea

<400> SEQUENCE: 48

Glu Arg Glu Arg Glu Glu Asp Trp Arg
1               5

<210> SEQ ID NO 49
<211> LENGTH: 12
<212> TYPE: PRT
<213> ORGANISM: Arachis hypogaea

<400> SEQUENCE: 49

Glu Arg Glu Arg Glu Glu Asp Trp Arg Gln Pro Arg
1               5                   10

<210> SEQ ID NO 50
<211> LENGTH: 21
<212> TYPE: PRT
<213> ORGANISM: Arachis hypogaea

<400> SEQUENCE: 50

Glu Ser His Phe Val Ser Ala Arg Pro Gln Ser Gln Ser Gln Ser Pro
1               5                   10                  15

Ser Ser Pro Glu Lys
            20

<210> SEQ ID NO 51
<211> LENGTH: 37
<212> TYPE: PRT
<213> ORGANISM: Arachis hypogaea

<400> SEQUENCE: 51

Glu Ser His Phe Val Ser Ala Arg Pro Gln Ser Gln Ser Gln Ser Pro
1               5                   10                  15

Ser Ser Pro Glu Lys Glu Ser Pro Glu Lys Glu Asp Gln Glu Glu Glu
            20                  25                  30

Asn Gln Gly Gly Lys
        35
```

<210> SEQ ID NO 52
<211> LENGTH: 16
<212> TYPE: PRT
<213> ORGANISM: Arachis hypogaea

<400> SEQUENCE: 52

Glu Ser Pro Glu Lys Glu Asp Gln Glu Glu Asn Gln Gly Gly Lys
1               5                   10                  15

<210> SEQ ID NO 53
<211> LENGTH: 8
<212> TYPE: PRT
<213> ORGANISM: Arachis hypogaea

<400> SEQUENCE: 53

Glu Val Arg Arg Tyr Thr Ala Arg
1               5

<210> SEQ ID NO 54
<211> LENGTH: 6
<212> TYPE: PRT
<213> ORGANISM: Arachis hypogaea

<400> SEQUENCE: 54

Phe Asp Gln Arg Ser Arg
1               5

<210> SEQ ID NO 55
<211> LENGTH: 15
<212> TYPE: PRT
<213> ORGANISM: Arachis hypogaea

<400> SEQUENCE: 55

Phe Asp Gln Arg Ser Arg Gln Phe Gln Asn Leu Gln Asn His Arg
1               5                   10                  15

<210> SEQ ID NO 56
<211> LENGTH: 11
<212> TYPE: PRT
<213> ORGANISM: Arachis hypogaea

<400> SEQUENCE: 56

Phe Ser Thr Arg Tyr Gly Asn Gln Asn Gly Arg
1               5                   10

<210> SEQ ID NO 57
<211> LENGTH: 13
<212> TYPE: PRT
<213> ORGANISM: Arachis hypogaea

<400> SEQUENCE: 57

Phe Ser Thr Arg Tyr Gly Asn Gln Asn Gly Arg Ile Arg
1               5                   10

<210> SEQ ID NO 58
<211> LENGTH: 13
<212> TYPE: PRT
<213> ORGANISM: Arachis hypogaea

<400> SEQUENCE: 58

Phe Ser Thr Arg Tyr Gly Asn Gln Asn Gly Arg Ile Arg
1               5                   10

```
<210> SEQ ID NO 59
<211> LENGTH: 17
<212> TYPE: PRT
<213> ORGANISM: Arachis hypogaea

<400> SEQUENCE: 59

Gly His Thr Gly Thr Thr Asn Gln Arg Ser Pro Pro Gly Glu Arg Thr
1               5                   10                  15

Arg

<210> SEQ ID NO 60
<211> LENGTH: 19
<212> TYPE: PRT
<213> ORGANISM: Arachis hypogaea

<400> SEQUENCE: 60

Gly His Thr Gly Thr Thr Asn Gln Arg Ser Pro Pro Gly Glu Arg Thr
1               5                   10                  15

Arg Gly Arg

<210> SEQ ID NO 61
<211> LENGTH: 8
<212> TYPE: PRT
<213> ORGANISM: Arachis hypogaea

<400> SEQUENCE: 61

Gly Gln Arg Arg Trp Ser Thr Arg
1               5

<210> SEQ ID NO 62
<211> LENGTH: 11
<212> TYPE: PRT
<213> ORGANISM: Arachis hypogaea

<400> SEQUENCE: 62

Gly Arg Gln Pro Gly Asp Tyr Asp Asp Asp Arg
1               5                   10

<210> SEQ ID NO 63
<211> LENGTH: 12
<212> TYPE: PRT
<213> ORGANISM: Arachis hypogaea

<400> SEQUENCE: 63

Gly Arg Gln Pro Gly Asp Tyr Asp Asp Asp Arg Arg
1               5                   10

<210> SEQ ID NO 64
<211> LENGTH: 15
<212> TYPE: PRT
<213> ORGANISM: Arachis hypogaea

<400> SEQUENCE: 64

Gly Arg Gln Pro Gly Asp Tyr Asp Asp Asp Arg Arg Gln Pro Arg
1               5                   10                  15

<210> SEQ ID NO 65
<211> LENGTH: 15
<212> TYPE: PRT
<213> ORGANISM: Arachis hypogaea

<400> SEQUENCE: 65

Gly Arg Gln Pro Gly Asp Tyr Asp Asp Asp Arg Arg Gln Pro Arg
1               5                   10                  15
```

<210> SEQ ID NO 66
<211> LENGTH: 18
<212> TYPE: PRT
<213> ORGANISM: Arachis hypogaea

<400> SEQUENCE: 66

Gly Arg Arg Glu Glu Glu Asp Glu Asp Glu Glu Glu Glu Gly Ser
1               5                   10                  15

Asn Arg

<210> SEQ ID NO 67
<211> LENGTH: 21
<212> TYPE: PRT
<213> ORGANISM: Arachis hypogaea

<400> SEQUENCE: 67

Gly Arg Arg Glu Glu Glu Asp Glu Asp Glu Glu Glu Glu Gly Ser
1               5                   10                  15

Asn Arg Glu Val Arg
            20

<210> SEQ ID NO 68
<211> LENGTH: 15
<212> TYPE: PRT
<213> ORGANISM: Arachis hypogaea

<400> SEQUENCE: 68

Gly Ser Glu Glu Glu Gly Asp Ile Thr Asn Pro Ile Asn Leu Arg
1               5                   10                  15

<210> SEQ ID NO 69
<211> LENGTH: 27
<212> TYPE: PRT
<213> ORGANISM: Arachis hypogaea

<400> SEQUENCE: 69

Gly Ser Glu Glu Glu Gly Asp Ile Thr Asn Pro Ile Asn Leu Arg Glu
1               5                   10                  15

Gly Glu Pro Asp Leu Ser Asn Asn Phe Gly Lys
            20                  25

<210> SEQ ID NO 70
<211> LENGTH: 11
<212> TYPE: PRT
<213> ORGANISM: Arachis hypogaea

<400> SEQUENCE: 70

Gly Thr Gly Asn Leu Glu Leu Val Ala Val Arg
1               5                   10

<210> SEQ ID NO 71
<211> LENGTH: 12
<212> TYPE: PRT
<213> ORGANISM: Arachis hypogaea

<400> SEQUENCE: 71

Gly Thr Gly Asn Leu Glu Leu Val Ala Val Arg Lys
1               5                   10

<210> SEQ ID NO 72
<211> LENGTH: 25
<212> TYPE: PRT

<213> ORGANISM: Arachis hypogaea

<400> SEQUENCE: 72

His Ala Asp Ala Asp Asn Ile Leu Val Ile Gln Gln Gly Gln Ala Thr
1               5                   10                  15

Val Thr Val Ala Asn Gly Asn Asn Arg
            20                  25

<210> SEQ ID NO 73
<211> LENGTH: 26
<212> TYPE: PRT
<213> ORGANISM: Arachis hypogaea

<400> SEQUENCE: 73

His Ala Asp Ala Asp Asn Ile Leu Val Ile Gln Gln Gly Gln Ala Thr
1               5                   10                  15

Val Thr Val Ala Asn Gly Asn Asn Arg Lys
            20                  25

<210> SEQ ID NO 74
<211> LENGTH: 37
<212> TYPE: PRT
<213> ORGANISM: Arachis hypogaea

<400> SEQUENCE: 74

His Ala Asp Ala Asp Asn Ile Leu Val Ile Gln Gln Gly Gln Ala Thr
1               5                   10                  15

Val Thr Val Ala Asn Gly Asn Asn Arg Lys Ser Phe Asn Leu Asp Glu
            20                  25                  30

Gly His Ala Leu Arg
        35

<210> SEQ ID NO 75
<211> LENGTH: 8
<212> TYPE: PRT
<213> ORGANISM: Arachis hypogaea

<400> SEQUENCE: 75

His Ala Lys Ser Val Ser Lys Lys
1               5

<210> SEQ ID NO 76
<211> LENGTH: 23
<212> TYPE: PRT
<213> ORGANISM: Arachis hypogaea

<400> SEQUENCE: 76

His Ala Lys Ser Val Ser Lys Lys Gly Ser Glu Glu Glu Gly Asp Ile
1               5                   10                  15

Thr Asn Pro Ile Asn Leu Arg
            20

<210> SEQ ID NO 77
<211> LENGTH: 7
<212> TYPE: PRT
<213> ORGANISM: Arachis hypogaea

<400> SEQUENCE: 77

His Asp Asn Gln Asn Leu Arg
1               5

<210> SEQ ID NO 78

```
<211> LENGTH: 30
<212> TYPE: PRT
<213> ORGANISM: Arachis hypogaea

<400> SEQUENCE: 78

His Asp Asn Gln Asn Leu Arg Val Ala Lys Ile Ser Met Pro Val Asn
1               5                   10                  15

Thr Pro Gly Gln Phe Glu Asp Phe Phe Pro Ala Ser Ser Arg
            20                  25                  30

<210> SEQ ID NO 79
<211> LENGTH: 16
<212> TYPE: PRT
<213> ORGANISM: Arachis hypogaea

<400> SEQUENCE: 79

Ile Phe Leu Ala Gly Asp Lys Asp Asn Val Ile Asp Gln Ile Glu Lys
1               5                   10                  15

<210> SEQ ID NO 80
<211> LENGTH: 19
<212> TYPE: PRT
<213> ORGANISM: Arachis hypogaea

<400> SEQUENCE: 80

Ile Phe Leu Ala Gly Asp Lys Asp Asn Val Ile Asp Gln Ile Glu Lys
1               5                   10                  15

Gln Ala Lys

<210> SEQ ID NO 81
<211> LENGTH: 32
<212> TYPE: PRT
<213> ORGANISM: Arachis hypogaea

<400> SEQUENCE: 81

Ile Phe Leu Ala Gly Asp Lys Asp Asn Val Ile Asp Gln Ile Glu Lys
1               5                   10                  15

Gln Ala Lys Asp Leu Ala Phe Pro Gly Ser Gly Glu Gln Val Glu Lys
            20                  25                  30

<210> SEQ ID NO 82
<211> LENGTH: 12
<212> TYPE: PRT
<213> ORGANISM: Arachis hypogaea

<400> SEQUENCE: 82

Ile Pro Ser Gly Phe Ile Ser Tyr Ile Leu Asn Arg
1               5                   10

<210> SEQ ID NO 83
<211> LENGTH: 19
<212> TYPE: PRT
<213> ORGANISM: Arachis hypogaea

<400> SEQUENCE: 83

Ile Pro Ser Gly Phe Ile Ser Tyr Ile Leu Asn Arg His Asp Asn Gln
1               5                   10                  15

Asn Leu Arg

<210> SEQ ID NO 84
<211> LENGTH: 22
<212> TYPE: PRT
<213> ORGANISM: Arachis hypogaea
```

```
<400> SEQUENCE: 84

Ile Pro Ser Gly Phe Ile Ser Tyr Ile Leu Asn Arg His Asp Asn Gln
1               5                   10                  15

Asn Leu Arg Val Ala Lys
            20

<210> SEQ ID NO 85
<211> LENGTH: 42
<212> TYPE: PRT
<213> ORGANISM: Arachis hypogaea

<400> SEQUENCE: 85

Ile Pro Ser Gly Phe Ile Ser Tyr Ile Leu Asn Arg His Asp Asn Gln
1               5                   10                  15

Asn Leu Arg Val Ala Lys Ile Ser Met Pro Val Asn Thr Pro Gly Gln
            20                  25                  30

Phe Glu Asp Phe Phe Pro Ala Ser Ser Arg
        35                  40

<210> SEQ ID NO 86
<211> LENGTH: 25
<212> TYPE: PRT
<213> ORGANISM: Arachis hypogaea

<400> SEQUENCE: 86

Ile Arg Pro Glu Gly Arg Glu Gly Glu Gln Glu Trp Gly Thr Pro Gly
1               5                   10                  15

Ser His Val Arg Glu Glu Thr Ser Arg
            20                  25

<210> SEQ ID NO 87
<211> LENGTH: 34
<212> TYPE: PRT
<213> ORGANISM: Arachis hypogaea

<400> SEQUENCE: 87

Ile Arg Pro Glu Gly Arg Glu Gly Glu Gln Glu Trp Gly Thr Pro Gly
1               5                   10                  15

Ser His Val Arg Glu Glu Thr Ser Arg Asn Asn Pro Phe Tyr Phe Pro
            20                  25                  30

Ser Arg

<210> SEQ ID NO 88
<211> LENGTH: 10
<212> TYPE: PRT
<213> ORGANISM: Arachis hypogaea

<400> SEQUENCE: 88

Ile Arg Val Leu Gln Arg Phe Asp Gln Arg
1               5                   10

<210> SEQ ID NO 89
<211> LENGTH: 20
<212> TYPE: PRT
<213> ORGANISM: Arachis hypogaea

<400> SEQUENCE: 89

Ile Ser Met Pro Val Asn Thr Pro Gly Gln Phe Glu Asp Phe Phe Pro
1               5                   10                  15

Ala Ser Ser Arg
```

20

<210> SEQ ID NO 90
<211> LENGTH: 31
<212> TYPE: PRT
<213> ORGANISM: Arachis hypogaea

<400> SEQUENCE: 90

Ile Ser Met Pro Val Asn Thr Pro Gly Gln Phe Glu Asp Phe Phe Pro
1               5                   10                  15

Ala Ser Ser Arg Asp Gln Ser Ser Tyr Leu Gln Gly Phe Ser Arg
            20                  25                  30

<210> SEQ ID NO 91
<211> LENGTH: 46
<212> TYPE: PRT
<213> ORGANISM: Arachis hypogaea

<400> SEQUENCE: 91

Ile Ser Met Pro Val Asn Thr Pro Gly Gln Phe Glu Asp Phe Phe Pro
1               5                   10                  15

Ala Ser Ser Arg Asp Gln Ser Ser Tyr Leu Gln Gly Phe Ser Arg Asn
            20                  25                  30

Thr Leu Glu Ala Ala Phe Asn Ala Glu Phe Asn Glu Ile Arg
        35                  40                  45

<210> SEQ ID NO 92
<211> LENGTH: 47
<212> TYPE: PRT
<213> ORGANISM: Arachis hypogaea

<400> SEQUENCE: 92

Ile Ser Met Pro Val Asn Thr Pro Gly Gln Phe Glu Asp Phe Phe Pro
1               5                   10                  15

Ala Ser Ser Arg Asp Gln Ser Ser Tyr Leu Gln Gly Phe Ser Arg Asn
            20                  25                  30

Thr Leu Glu Ala Ala Phe Asn Ala Glu Phe Asn Glu Ile Arg Arg
        35                  40                  45

<210> SEQ ID NO 93
<211> LENGTH: 15
<212> TYPE: PRT
<213> ORGANISM: Arachis hypogaea

<400> SEQUENCE: 93

Ile Val Gln Ile Glu Ala Lys Pro Asn Thr Leu Val Leu Pro Lys
1               5                   10                  15

<210> SEQ ID NO 94
<211> LENGTH: 6
<212> TYPE: PRT
<213> ORGANISM: Arachis hypogaea

<400> SEQUENCE: 94

Lys Glu Gln Gln Gln Arg
1               5

<210> SEQ ID NO 95
<211> LENGTH: 9
<212> TYPE: PRT
<213> ORGANISM: Arachis hypogaea

<400> SEQUENCE: 95

Lys Glu Gln Gln Gln Arg Gly Arg Arg
1               5

<210> SEQ ID NO 96
<211> LENGTH: 16
<212> TYPE: PRT
<213> ORGANISM: Arachis hypogaea

<400> SEQUENCE: 96

Lys Gly Ser Glu Glu Glu Gly Asp Ile Thr Asn Pro Ile Asn Leu Arg
1               5                   10                  15

<210> SEQ ID NO 97
<211> LENGTH: 28
<212> TYPE: PRT
<213> ORGANISM: Arachis hypogaea

<400> SEQUENCE: 97

Lys Gly Ser Glu Glu Glu Gly Asp Ile Thr Asn Pro Ile Asn Leu Arg
1               5                   10                  15

Glu Gly Glu Pro Asp Leu Ser Asn Asn Phe Gly Lys
            20                  25

<210> SEQ ID NO 98
<211> LENGTH: 36
<212> TYPE: PRT
<213> ORGANISM: Arachis hypogaea

<400> SEQUENCE: 98

Lys Gly Ser Glu Glu Glu Gly Asp Ile Thr Asn Pro Ile Asn Leu Arg
1               5                   10                  15

Glu Gly Glu Pro Asp Leu Ser Asn Asn Phe Gly Lys Leu Phe Glu Val
            20                  25                  30

Lys Pro Asp Lys
        35

<210> SEQ ID NO 99
<211> LENGTH: 26
<212> TYPE: PRT
<213> ORGANISM: Arachis hypogaea

<400> SEQUENCE: 99

Lys Ile Arg Pro Glu Gly Arg Glu Gly Glu Gln Glu Trp Gly Thr Pro
1               5                   10                  15

Gly Ser His Val Arg Glu Glu Thr Ser Arg
            20                  25

<210> SEQ ID NO 100
<211> LENGTH: 18
<212> TYPE: PRT
<213> ORGANISM: Arachis hypogaea

<400> SEQUENCE: 100

Lys Asn Pro Gln Leu Gln Asp Leu Asp Met Met Leu Thr Cys Val Glu
1               5                   10                  15

Ile Lys

<210> SEQ ID NO 101
<211> LENGTH: 30
<212> TYPE: PRT
<213> ORGANISM: Arachis hypogaea

```
<400> SEQUENCE: 101

Lys Asn Pro Gln Leu Gln Asp Leu Asp Met Met Leu Thr Cys Val Glu
1               5                   10                  15

Ile Lys Glu Gly Ala Leu Met Leu Pro His Phe Asn Ser Lys
            20                  25                  30

<210> SEQ ID NO 102
<211> LENGTH: 39
<212> TYPE: PRT
<213> ORGANISM: Arachis hypogaea

<400> SEQUENCE: 102

Lys Asn Pro Gln Leu Gln Asp Leu Asp Met Met Leu Thr Cys Val Glu
1               5                   10                  15

Ile Lys Glu Gly Ala Leu Met Leu Pro His Phe Asn Ser Lys Ala Met
            20                  25                  30

Val Ile Val Val Val Asn Lys
        35

<210> SEQ ID NO 103
<211> LENGTH: 12
<212> TYPE: PRT
<213> ORGANISM: Arachis hypogaea

<400> SEQUENCE: 103

Lys Ser Phe Asn Leu Asp Glu Gly His Ala Leu Arg
1               5                   10

<210> SEQ ID NO 104
<211> LENGTH: 24
<212> TYPE: PRT
<213> ORGANISM: Arachis hypogaea

<400> SEQUENCE: 104

Lys Ser Phe Asn Leu Asp Glu Gly His Ala Leu Arg Ile Pro Ser Gly
1               5                   10                  15

Phe Ile Ser Tyr Ile Leu Asn Arg
            20

<210> SEQ ID NO 105
<211> LENGTH: 31
<212> TYPE: PRT
<213> ORGANISM: Arachis hypogaea

<400> SEQUENCE: 105

Lys Ser Phe Asn Leu Asp Glu Gly His Ala Leu Arg Ile Pro Ser Gly
1               5                   10                  15

Phe Ile Ser Tyr Ile Leu Asn Arg His Asp Asn Gln Asn Leu Arg
            20                  25                  30

<210> SEQ ID NO 106
<211> LENGTH: 9
<212> TYPE: PRT
<213> ORGANISM: Arachis hypogaea

<400> SEQUENCE: 106

Lys Thr Glu Asn Pro Cys Ala Gln Arg
1               5

<210> SEQ ID NO 107
<211> LENGTH: 22
<212> TYPE: PRT
```

<213> ORGANISM: Arachis hypogaea

<400> SEQUENCE: 107

Lys Thr Glu Asn Pro Cys Ala Gln Arg Cys Leu Gln Ser Cys Gln Gln
1               5                   10                  15

Glu Pro Asp Asp Leu Lys
            20

<210> SEQ ID NO 108
<211> LENGTH: 24
<212> TYPE: PRT
<213> ORGANISM: Arachis hypogaea

<400> SEQUENCE: 108

Lys Thr Glu Asn Pro Cys Ala Gln Arg Cys Leu Gln Ser Cys Gln Gln
1               5                   10                  15

Glu Pro Asp Asp Leu Lys Gln Lys
            20

<210> SEQ ID NO 109
<211> LENGTH: 6
<212> TYPE: PRT
<213> ORGANISM: Arachis hypogaea

<400> SEQUENCE: 109

Leu Glu Tyr Asp Pro Arg
1               5

<210> SEQ ID NO 110
<211> LENGTH: 12
<212> TYPE: PRT
<213> ORGANISM: Arachis hypogaea

<400> SEQUENCE: 110

Leu Glu Tyr Asp Pro Arg Cys Val Tyr Asp Pro Arg
1               5                   10

<210> SEQ ID NO 111
<211> LENGTH: 21
<212> TYPE: PRT
<213> ORGANISM: Arachis hypogaea

<400> SEQUENCE: 111

Leu Glu Tyr Asp Pro Arg Cys Val Tyr Asp Pro Arg Gly His Thr Gly
1               5                   10                  15

Thr Thr Asn Gln Arg
            20

<210> SEQ ID NO 112
<211> LENGTH: 27
<212> TYPE: PRT
<213> ORGANISM: Arachis hypogaea

<400> SEQUENCE: 112

Leu Glu Tyr Asp Pro Arg Cys Val Tyr Asp Pro Arg Gly His Thr Gly
1               5                   10                  15

Thr Thr Asn Gln Arg Ser Pro Pro Gly Glu Arg
            20                  25

<210> SEQ ID NO 113
<211> LENGTH: 8
<212> TYPE: PRT
<213> ORGANISM: Arachis hypogaea

```
<400> SEQUENCE: 113

Leu Phe Glu Val Lys Pro Asp Lys
1               5

<210> SEQ ID NO 114
<211> LENGTH: 9
<212> TYPE: PRT
<213> ORGANISM: Arachis hypogaea

<400> SEQUENCE: 114

Leu Phe Glu Val Lys Pro Asp Lys Lys
1               5

<210> SEQ ID NO 115
<211> LENGTH: 26
<212> TYPE: PRT
<213> ORGANISM: Arachis hypogaea

<400> SEQUENCE: 115

Leu Phe Glu Val Lys Pro Asp Lys Lys Asn Pro Gln Leu Gln Asp Leu
1               5                   10                  15

Asp Met Met Leu Thr Cys Val Glu Ile Lys
            20                  25

<210> SEQ ID NO 116
<211> LENGTH: 38
<212> TYPE: PRT
<213> ORGANISM: Arachis hypogaea

<400> SEQUENCE: 116

Leu Phe Glu Val Lys Pro Asp Lys Lys Asn Pro Gln Leu Gln Asp Leu
1               5                   10                  15

Asp Met Met Leu Thr Cys Val Glu Ile Lys Glu Gly Ala Leu Met Leu
            20                  25                  30

Pro His Phe Asn Ser Lys
        35

<210> SEQ ID NO 117
<211> LENGTH: 27
<212> TYPE: PRT
<213> ORGANISM: Arachis hypogaea

<400> SEQUENCE: 117

Leu Ile Lys Asn Gln Lys Glu Ser His Phe Val Ser Ala Arg Pro Gln
1               5                   10                  15

Ser Gln Ser Gln Ser Pro Ser Ser Pro Glu Lys
            20                  25

<210> SEQ ID NO 118
<211> LENGTH: 9
<212> TYPE: PRT
<213> ORGANISM: Arachis hypogaea

<400> SEQUENCE: 118

Asn Asn Pro Phe Tyr Phe Pro Ser Arg
1               5

<210> SEQ ID NO 119
<211> LENGTH: 10
<212> TYPE: PRT
<213> ORGANISM: Arachis hypogaea
```

-continued

```
<400> SEQUENCE: 119

Asn Asn Pro Phe Tyr Phe Pro Ser Arg Arg
1               5                   10

<210> SEQ ID NO 120
<211> LENGTH: 14
<212> TYPE: PRT
<213> ORGANISM: Arachis hypogaea

<400> SEQUENCE: 120

Asn Asn Pro Phe Tyr Phe Pro Ser Arg Arg Phe Ser Thr Arg
1               5                   10

<210> SEQ ID NO 121
<211> LENGTH: 21
<212> TYPE: PRT
<213> ORGANISM: Arachis hypogaea

<400> SEQUENCE: 121

Asn Asn Pro Phe Tyr Phe Pro Ser Arg Arg Phe Ser Thr Arg Tyr Gly
1               5                   10                  15

Asn Gln Asn Gly Arg
            20

<210> SEQ ID NO 122
<211> LENGTH: 17
<212> TYPE: PRT
<213> ORGANISM: Arachis hypogaea

<400> SEQUENCE: 122

Asn Pro Gln Leu Gln Asp Leu Asp Met Met Leu Thr Cys Val Glu Ile
1               5                   10                  15

Lys

<210> SEQ ID NO 123
<211> LENGTH: 29
<212> TYPE: PRT
<213> ORGANISM: Arachis hypogaea

<400> SEQUENCE: 123

Asn Pro Gln Leu Gln Asp Leu Asp Met Met Leu Thr Cys Val Glu Ile
1               5                   10                  15

Lys Glu Gly Ala Leu Met Leu Pro His Phe Asn Ser Lys
            20                  25

<210> SEQ ID NO 124
<211> LENGTH: 38
<212> TYPE: PRT
<213> ORGANISM: Arachis hypogaea

<400> SEQUENCE: 124

Asn Pro Gln Leu Gln Asp Leu Asp Met Met Leu Thr Cys Val Glu Ile
1               5                   10                  15

Lys Glu Gly Ala Leu Met Leu Pro His Phe Asn Ser Lys Ala Met Val
            20                  25                  30

Ile Val Val Val Asn Lys
        35

<210> SEQ ID NO 125
<211> LENGTH: 24
<212> TYPE: PRT
<213> ORGANISM: Arachis hypogaea
```

```
<400> SEQUENCE: 125

Asn Gln Lys Glu Ser His Phe Val Ser Ala Arg Pro Gln Ser Gln Ser
1               5                   10                  15

Gln Ser Pro Ser Ser Pro Glu Lys
            20

<210> SEQ ID NO 126
<211> LENGTH: 40
<212> TYPE: PRT
<213> ORGANISM: Arachis hypogaea

<400> SEQUENCE: 126

Asn Gln Lys Glu Ser His Phe Val Ser Ala Arg Pro Gln Ser Gln Ser
1               5                   10                  15

Gln Ser Pro Ser Ser Pro Glu Lys Glu Ser Pro Glu Lys Glu Asp Gln
            20                  25                  30

Glu Glu Glu Asn Gln Gly Gly Lys
        35                  40

<210> SEQ ID NO 127
<211> LENGTH: 15
<212> TYPE: PRT
<213> ORGANISM: Arachis hypogaea

<400> SEQUENCE: 127

Asn Thr Leu Glu Ala Ala Phe Asn Ala Glu Phe Asn Glu Ile Arg
1               5                   10                  15

<210> SEQ ID NO 128
<211> LENGTH: 16
<212> TYPE: PRT
<213> ORGANISM: Arachis hypogaea

<400> SEQUENCE: 128

Asn Thr Leu Glu Ala Ala Phe Asn Ala Glu Phe Asn Glu Ile Arg Arg
1               5                   10                  15

<210> SEQ ID NO 129
<211> LENGTH: 30
<212> TYPE: PRT
<213> ORGANISM: Arachis hypogaea

<400> SEQUENCE: 129

Asn Thr Leu Glu Ala Ala Phe Asn Ala Glu Phe Asn Glu Ile Arg Arg
1               5                   10                  15

Val Leu Leu Glu Glu Asn Ala Gly Gly Glu Gln Glu Glu Arg
            20                  25                  30

<210> SEQ ID NO 130
<211> LENGTH: 33
<212> TYPE: PRT
<213> ORGANISM: Arachis hypogaea

<400> SEQUENCE: 130

Asn Thr Leu Glu Ala Ala Phe Asn Ala Glu Phe Asn Glu Ile Arg Arg
1               5                   10                  15

Val Leu Leu Glu Glu Asn Ala Gly Gly Glu Gln Glu Glu Arg Gly Gln
            20                  25                  30

Arg
```

```
<210> SEQ ID NO 131
<211> LENGTH: 16
<212> TYPE: PRT
<213> ORGANISM: Arachis hypogaea

<400> SEQUENCE: 131

Gln Ala Lys Asp Leu Ala Phe Pro Gly Ser Gly Glu Gln Val Glu Lys
1               5                   10                  15

<210> SEQ ID NO 132
<211> LENGTH: 9
<212> TYPE: PRT
<213> ORGANISM: Arachis hypogaea

<400> SEQUENCE: 132

Gln Phe Gln Asn Leu Gln Asn His Arg
1               5

<210> SEQ ID NO 133
<211> LENGTH: 50
<212> TYPE: PRT
<213> ORGANISM: Arachis hypogaea

<400> SEQUENCE: 133

Gln Phe Gln Asn Leu Gln Asn His Arg Ile Val Gln Ile Glu Ala Lys
1               5                   10                  15

Pro Asn Thr Leu Val Leu Pro Lys His Ala Asp Ala Asp Asn Ile Leu
            20                  25                  30

Val Ile Gln Gln Gly Gln Ala Thr Val Thr Val Ala Asn Gly Asn Asn
        35                  40                  45

Arg Lys
    50

<210> SEQ ID NO 134
<211> LENGTH: 7
<212> TYPE: PRT
<213> ORGANISM: Arachis hypogaea

<400> SEQUENCE: 134

Gln Lys Ala Cys Glu Ser Arg
1               5

<210> SEQ ID NO 135
<211> LENGTH: 16
<212> TYPE: PRT
<213> ORGANISM: Arachis hypogaea

<400> SEQUENCE: 135

Gln Lys Ala Cys Glu Ser Arg Cys Thr Lys Leu Glu Tyr Asp Pro Arg
1               5                   10                  15

<210> SEQ ID NO 136
<211> LENGTH: 10
<212> TYPE: PRT
<213> ORGANISM: Arachis hypogaea

<400> SEQUENCE: 136

Gln Pro Gly Asp Tyr Asp Asp Asp Arg Arg
1               5                   10

<210> SEQ ID NO 137
<211> LENGTH: 13
<212> TYPE: PRT
<213> ORGANISM: Arachis hypogaea
```

-continued

<400> SEQUENCE: 137

Gln Pro Gly Asp Tyr Asp Asp Arg Arg Gln Pro Arg
1               5                   10

<210> SEQ ID NO 138
<211> LENGTH: 14
<212> TYPE: PRT
<213> ORGANISM: Arachis hypogaea

<400> SEQUENCE: 138

Gln Pro Gly Asp Tyr Asp Asp Arg Arg Gln Pro Arg Arg
1               5                   10

<210> SEQ ID NO 139
<211> LENGTH: 15
<212> TYPE: PRT
<213> ORGANISM: Arachis hypogaea

<400> SEQUENCE: 139

Gln Pro Arg Glu Asp Trp Arg Arg Pro Ser His Gln Gln Pro Arg
1               5                   10                  15

<210> SEQ ID NO 140
<211> LENGTH: 16
<212> TYPE: PRT
<213> ORGANISM: Arachis hypogaea

<400> SEQUENCE: 140

Gln Pro Arg Glu Asp Trp Arg Arg Pro Ser His Gln Gln Pro Arg Lys
1               5                   10                  15

<210> SEQ ID NO 141
<211> LENGTH: 9
<212> TYPE: PRT
<213> ORGANISM: Arachis hypogaea

<400> SEQUENCE: 141

Gln Pro Arg Arg Glu Glu Gly Gly Arg
1               5

<210> SEQ ID NO 142
<211> LENGTH: 16
<212> TYPE: PRT
<213> ORGANISM: Arachis hypogaea

<400> SEQUENCE: 142

Gln Pro Arg Arg Glu Glu Gly Gly Arg Trp Gly Pro Ala Gly Pro Arg
1               5                   10                  15

<210> SEQ ID NO 143
<211> LENGTH: 16
<212> TYPE: PRT
<213> ORGANISM: Arachis hypogaea

<400> SEQUENCE: 143

Arg Glu Glu Glu Glu Asp Glu Asp Glu Glu Glu Gly Ser Asn Arg
1               5                   10                  15

<210> SEQ ID NO 144
<211> LENGTH: 19
<212> TYPE: PRT
<213> ORGANISM: Arachis hypogaea

<400> SEQUENCE: 144

```
Arg Glu Glu Glu Glu Asp Glu Asp Glu Glu Glu Gly Ser Asn Arg
1               5                   10                  15

Glu Val Arg

<210> SEQ ID NO 145
<211> LENGTH: 20
<212> TYPE: PRT
<213> ORGANISM: Arachis hypogaea

<400> SEQUENCE: 145

Arg Glu Glu Glu Glu Asp Glu Asp Glu Glu Glu Gly Ser Asn Arg
1               5                   10                  15

Glu Val Arg Arg
            20

<210> SEQ ID NO 146
<211> LENGTH: 6
<212> TYPE: PRT
<213> ORGANISM: Arachis hypogaea

<400> SEQUENCE: 146

Arg Glu Glu Gly Gly Arg
1               5

<210> SEQ ID NO 147
<211> LENGTH: 13
<212> TYPE: PRT
<213> ORGANISM: Arachis hypogaea

<400> SEQUENCE: 147

Arg Glu Glu Gly Gly Arg Trp Gly Pro Ala Gly Pro Arg
1               5                   10

<210> SEQ ID NO 148
<211> LENGTH: 15
<212> TYPE: PRT
<213> ORGANISM: Arachis hypogaea

<400> SEQUENCE: 148

Arg Glu Glu Gly Gly Arg Trp Gly Pro Ala Gly Pro Arg Glu Arg
1               5                   10                  15

<210> SEQ ID NO 149
<211> LENGTH: 12
<212> TYPE: PRT
<213> ORGANISM: Arachis hypogaea

<400> SEQUENCE: 149

Arg Phe Ser Thr Arg Tyr Gly Asn Gln Asn Gly Arg
1               5                   10

<210> SEQ ID NO 150
<211> LENGTH: 14
<212> TYPE: PRT
<213> ORGANISM: Arachis hypogaea

<400> SEQUENCE: 150

Arg Phe Ser Thr Arg Tyr Gly Asn Gln Asn Gly Arg Ile Arg
1               5                   10

<210> SEQ ID NO 151
<211> LENGTH: 8
<212> TYPE: PRT
```

<213> ORGANISM: Arachis hypogaea

<400> SEQUENCE: 151

Arg Pro Ser His Gln Gln Pro Arg
1               5

<210> SEQ ID NO 152
<211> LENGTH: 15
<212> TYPE: PRT
<213> ORGANISM: Arachis hypogaea

<400> SEQUENCE: 152

Arg Val Leu Leu Glu Glu Asn Ala Gly Gly Glu Gln Glu Glu Arg
1               5                   10                  15

<210> SEQ ID NO 153
<211> LENGTH: 18
<212> TYPE: PRT
<213> ORGANISM: Arachis hypogaea

<400> SEQUENCE: 153

Arg Val Leu Leu Glu Glu Asn Ala Gly Gly Glu Gln Glu Glu Arg Gly
1               5                   10                  15

Gln Arg

<210> SEQ ID NO 154
<211> LENGTH: 16
<212> TYPE: PRT
<213> ORGANISM: Arachis hypogaea

<400> SEQUENCE: 154

Arg Trp Ser Thr Arg Ser Ser Glu Asn Asn Glu Gly Val Ile Val Lys
1               5                   10                  15

<210> SEQ ID NO 155
<211> LENGTH: 11
<212> TYPE: PRT
<213> ORGANISM: Arachis hypogaea

<400> SEQUENCE: 155

Ser Phe Asn Leu Asp Glu Gly His Ala Leu Arg
1               5                   10

<210> SEQ ID NO 156
<211> LENGTH: 23
<212> TYPE: PRT
<213> ORGANISM: Arachis hypogaea

<400> SEQUENCE: 156

Ser Phe Asn Leu Asp Glu Gly His Ala Leu Arg Ile Pro Ser Gly Phe
1               5                   10                  15

Ile Ser Tyr Ile Leu Asn Arg
            20

<210> SEQ ID NO 157
<211> LENGTH: 30
<212> TYPE: PRT
<213> ORGANISM: Arachis hypogaea

<400> SEQUENCE: 157

Ser Phe Asn Leu Asp Glu Gly His Ala Leu Arg Ile Pro Ser Gly Phe
1               5                   10                  15

Ile Ser Tyr Ile Leu Asn Arg His Asp Asn Gln Asn Leu Arg

<210> SEQ ID NO 158
<211> LENGTH: 10
<212> TYPE: PRT
<213> ORGANISM: Arachis hypogaea

<400> SEQUENCE: 158

Ser Pro Pro Gly Glu Arg Thr Arg Gly Arg
1               5                   10

<210> SEQ ID NO 159
<211> LENGTH: 19
<212> TYPE: PRT
<213> ORGANISM: Arachis hypogaea

<400> SEQUENCE: 159

Ser Pro Pro Gly Glu Arg Thr Arg Gly Arg Gln Pro Gly Asp Tyr Asp
1               5                   10                  15

Asp Asp Arg

<210> SEQ ID NO 160
<211> LENGTH: 11
<212> TYPE: PRT
<213> ORGANISM: Arachis hypogaea

<400> SEQUENCE: 160

Ser Arg Gln Phe Gln Asn Leu Gln Asn His Arg
1               5                   10

<210> SEQ ID NO 161
<211> LENGTH: 51
<212> TYPE: PRT
<213> ORGANISM: Arachis hypogaea

<400> SEQUENCE: 161

Ser Arg Gln Phe Gln Asn Leu Gln Asn His Arg Ile Val Gln Ile Glu
1               5                   10                  15

Ala Lys Pro Asn Thr Leu Val Leu Pro Lys His Ala Asp Ala Asp Asn
                20                  25                  30

Ile Leu Val Ile Gln Gln Gly Gln Ala Thr Val Thr Val Ala Asn Gly
            35                  40                  45

Asn Asn Arg
        50

<210> SEQ ID NO 162
<211> LENGTH: 11
<212> TYPE: PRT
<213> ORGANISM: Arachis hypogaea

<400> SEQUENCE: 162

Ser Ser Glu Asn Asn Glu Gly Val Ile Val Lys
1               5                   10

<210> SEQ ID NO 163
<211> LENGTH: 14
<212> TYPE: PRT
<213> ORGANISM: Arachis hypogaea

<400> SEQUENCE: 163

Ser Ser Glu Asn Asn Glu Gly Val Ile Val Lys Val Ser Lys
1               5                   10

<210> SEQ ID NO 164
<211> LENGTH: 22
<212> TYPE: PRT
<213> ORGANISM: Arachis hypogaea

<400> SEQUENCE: 164

Ser Ser Glu Asn Asn Glu Gly Val Ile Val Lys Val Ser Lys Glu His
1               5                   10                  15

Val Glu Glu Leu Thr Lys
            20

<210> SEQ ID NO 165
<211> LENGTH: 7
<212> TYPE: PRT
<213> ORGANISM: Arachis hypogaea

<400> SEQUENCE: 165

Ser Ser Pro Tyr Gln Lys Lys
1               5

<210> SEQ ID NO 166
<211> LENGTH: 15
<212> TYPE: PRT
<213> ORGANISM: Arachis hypogaea

<400> SEQUENCE: 166

Ser Ser Pro Tyr Gln Lys Lys Thr Glu Asn Pro Cys Ala Gln Arg
1               5                   10                  15

<210> SEQ ID NO 167
<211> LENGTH: 28
<212> TYPE: PRT
<213> ORGANISM: Arachis hypogaea

<400> SEQUENCE: 167

Ser Ser Pro Tyr Gln Lys Lys Thr Glu Asn Pro Cys Ala Gln Arg Cys
1               5                   10                  15

Leu Gln Ser Cys Gln Gln Glu Pro Asp Asp Leu Lys
            20                  25

<210> SEQ ID NO 168
<211> LENGTH: 20
<212> TYPE: PRT
<213> ORGANISM: Arachis hypogaea

<400> SEQUENCE: 168

Ser Val Ser Lys Lys Gly Ser Glu Glu Glu Gly Asp Ile Thr Asn Pro
1               5                   10                  15

Ile Asn Leu Arg
            20

<210> SEQ ID NO 169
<211> LENGTH: 8
<212> TYPE: PRT
<213> ORGANISM: Arachis hypogaea

<400> SEQUENCE: 169

Thr Glu Asn Pro Cys Ala Gln Arg
1               5

<210> SEQ ID NO 170
<211> LENGTH: 21
<212> TYPE: PRT

<213> ORGANISM: Arachis hypogaea

<400> SEQUENCE: 170

Thr Glu Asn Pro Cys Ala Gln Arg Cys Leu Gln Ser Cys Gln Gln Glu
1               5                   10                  15

Pro Asp Asp Leu Lys
            20

<210> SEQ ID NO 171
<211> LENGTH: 23
<212> TYPE: PRT
<213> ORGANISM: Arachis hypogaea

<400> SEQUENCE: 171

Thr Glu Asn Pro Cys Ala Gln Arg Cys Leu Gln Ser Cys Gln Gln Glu
1               5                   10                  15

Pro Asp Asp Leu Lys Gln Lys
            20

<210> SEQ ID NO 172
<211> LENGTH: 28
<212> TYPE: PRT
<213> ORGANISM: Arachis hypogaea

<400> SEQUENCE: 172

Thr Glu Asn Pro Cys Ala Gln Arg Cys Leu Gln Ser Cys Gln Gln Glu
1               5                   10                  15

Pro Asp Asp Leu Lys Gln Lys Ala Cys Glu Ser Arg
            20                  25

<210> SEQ ID NO 173
<211> LENGTH: 13
<212> TYPE: PRT
<213> ORGANISM: Arachis hypogaea

<400> SEQUENCE: 173

Thr Arg Gly Arg Gln Pro Gly Asp Tyr Asp Asp Asp Arg
1               5                   10

<210> SEQ ID NO 174
<211> LENGTH: 14
<212> TYPE: PRT
<213> ORGANISM: Arachis hypogaea

<400> SEQUENCE: 174

Thr Arg Gly Arg Gln Pro Gly Asp Tyr Asp Asp Asp Arg Arg
1               5                   10

<210> SEQ ID NO 175
<211> LENGTH: 23
<212> TYPE: PRT
<213> ORGANISM: Arachis hypogaea

<400> SEQUENCE: 175

Val Ala Lys Ile Ser Met Pro Val Asn Thr Pro Gly Gln Phe Glu Asp
1               5                   10                  15

Phe Phe Pro Ala Ser Ser Arg
            20

<210> SEQ ID NO 176
<211> LENGTH: 49
<212> TYPE: PRT
<213> ORGANISM: Arachis hypogaea

<400> SEQUENCE: 176

Val Ala Lys Ile Ser Met Pro Val Asn Thr Pro Gly Gln Phe Glu Asp
1               5                   10                  15
Phe Phe Pro Ala Ser Ser Arg Asp Gln Ser Ser Tyr Leu Gln Gly Phe
            20                  25                  30
Ser Arg Asn Thr Leu Glu Ala Ala Phe Asn Ala Glu Phe Asn Glu Ile
        35                  40                  45
Arg

<210> SEQ ID NO 177
<211> LENGTH: 14
<212> TYPE: PRT
<213> ORGANISM: Arachis hypogaea

<400> SEQUENCE: 177

Val Leu Leu Glu Glu Asn Ala Gly Gly Glu Gln Glu Glu Arg
1               5                   10

<210> SEQ ID NO 178
<211> LENGTH: 17
<212> TYPE: PRT
<213> ORGANISM: Arachis hypogaea

<400> SEQUENCE: 178

Val Leu Leu Glu Glu Asn Ala Gly Gly Glu Gln Glu Glu Arg Gly Gln
1               5                   10                  15
Arg

<210> SEQ ID NO 179
<211> LENGTH: 18
<212> TYPE: PRT
<213> ORGANISM: Arachis hypogaea

<400> SEQUENCE: 179

Val Leu Leu Glu Glu Asn Ala Gly Gly Glu Gln Glu Glu Arg Gly Gln
1               5                   10                  15
Arg Arg

<210> SEQ ID NO 180
<211> LENGTH: 22
<212> TYPE: PRT
<213> ORGANISM: Arachis hypogaea

<400> SEQUENCE: 180

Val Leu Leu Glu Glu Asn Ala Gly Gly Glu Gln Glu Glu Arg Gly Gln
1               5                   10                  15
Arg Arg Trp Ser Thr Arg
            20

<210> SEQ ID NO 181
<211> LENGTH: 19
<212> TYPE: PRT
<213> ORGANISM: Arachis hypogaea

<400> SEQUENCE: 181

Val Leu Gln Arg Phe Asp Gln Arg Ser Arg Gln Phe Gln Asn Leu Gln
1               5                   10                  15
Asn His Arg

```
<210> SEQ ID NO 182
<211> LENGTH: 11
<212> TYPE: PRT
<213> ORGANISM: Arachis hypogaea

<400> SEQUENCE: 182

Val Ser Lys Glu His Val Glu Glu Leu Thr Lys
1               5                   10

<210> SEQ ID NO 183
<211> LENGTH: 22
<212> TYPE: PRT
<213> ORGANISM: Arachis hypogaea

<400> SEQUENCE: 183

Val Ser Pro Leu Met Leu Leu Gly Ile Leu Val Leu Ala Ser Val
1               5                   10                  15

Ser Ala Thr His Ala Lys
            20

<210> SEQ ID NO 184
<211> LENGTH: 7
<212> TYPE: PRT
<213> ORGANISM: Arachis hypogaea

<400> SEQUENCE: 184

Trp Gly Pro Ala Gly Pro Arg
1               5

<210> SEQ ID NO 185
<211> LENGTH: 9
<212> TYPE: PRT
<213> ORGANISM: Arachis hypogaea

<400> SEQUENCE: 185

Trp Gly Pro Ala Gly Pro Arg Glu Arg
1               5

<210> SEQ ID NO 186
<211> LENGTH: 11
<212> TYPE: PRT
<213> ORGANISM: Arachis hypogaea

<400> SEQUENCE: 186

Trp Gly Pro Ala Gly Pro Arg Glu Arg Glu Arg
1               5                   10

<210> SEQ ID NO 187
<211> LENGTH: 15
<212> TYPE: PRT
<213> ORGANISM: Arachis hypogaea

<400> SEQUENCE: 187

Trp Ser Thr Arg Ser Ser Glu Asn Asn Glu Gly Val Ile Val Lys
1               5                   10                  15

<210> SEQ ID NO 188
<211> LENGTH: 26
<212> TYPE: PRT
<213> ORGANISM: Arachis hypogaea

<400> SEQUENCE: 188

Trp Ser Thr Arg Ser Ser Glu Asn Asn Glu Gly Val Ile Val Lys Val
1               5                   10                  15
```

Ser Lys Glu His Val Glu Glu Leu Thr Lys
            20                  25

<210> SEQ ID NO 189
<211> LENGTH: 7
<212> TYPE: PRT
<213> ORGANISM: Arachis hypogaea

<400> SEQUENCE: 189

Tyr Gly Asn Gln Asn Gly Arg
1               5

<210> SEQ ID NO 190
<211> LENGTH: 13
<212> TYPE: PRT
<213> ORGANISM: Arachis hypogaea

<400> SEQUENCE: 190

Tyr Gly Asn Gln Asn Gly Arg Ile Arg Val Leu Gln Arg
1               5                   10

<210> SEQ ID NO 191
<211> LENGTH: 17
<212> TYPE: PRT
<213> ORGANISM: Arachis hypogaea

<400> SEQUENCE: 191

Tyr Gly Asn Gln Asn Gly Arg Ile Arg Val Leu Gln Arg Phe Asp Gln
1               5                   10                  15

Arg

<210> SEQ ID NO 192
<211> LENGTH: 48
<212> TYPE: PRT
<213> ORGANISM: Arachis hypogaea

<400> SEQUENCE: 192

Tyr Thr Ala Arg Leu Lys Glu Gly Asp Val Phe Ile Met Pro Ala Ala
1               5                   10                  15

His Pro Val Ala Ile Asn Ala Ser Ser Glu Leu His Leu Leu Gly Phe
            20                  25                  30

Gly Ile Asn Ala Glu Asn Asn His Arg Ile Phe Leu Ala Gly Asp Lys
        35                  40                  45

<210> SEQ ID NO 193
<211> LENGTH: 18
<212> TYPE: PRT
<213> ORGANISM: Arachis hypogaea

<400> SEQUENCE: 193

Glu Gln Glu Trp Glu Glu Glu Glu Asp Glu Glu Glu Glu Gly Ser
1               5                   10                  15

Asn Arg

<210> SEQ ID NO 194
<211> LENGTH: 14
<212> TYPE: PRT
<213> ORGANISM: Arachis hypogaea

<400> SEQUENCE: 194

Gly Ser Glu Glu Glu Asp Ile Thr Asn Pro Ile Asn Leu Arg
1               5                   10

<210> SEQ ID NO 195
<211> LENGTH: 14
<212> TYPE: PRT
<213> ORGANISM: Arachis hypogaea

<400> SEQUENCE: 195

Glu Gly Glu Gln Glu Trp Gly Thr Pro Gly Ser Glu Val Arg
1               5                   10

<210> SEQ ID NO 196
<211> LENGTH: 15
<212> TYPE: PRT
<213> ORGANISM: Arachis hypogaea

<400> SEQUENCE: 196

Ile Val Gln Ile Glu Ala Arg Pro Asn Thr Leu Val Leu Pro Lys
1               5                   10                  15

<210> SEQ ID NO 197
<211> LENGTH: 10
<212> TYPE: PRT
<213> ORGANISM: Arachis hypogaea

<400> SEQUENCE: 197

Gly Ala Gly Ser Ser Gln His Gln Glu Arg
1               5                   10

<210> SEQ ID NO 198
<211> LENGTH: 7
<212> TYPE: PRT
<213> ORGANISM: Arachis hypogaea

<400> SEQUENCE: 198

Gln Gln Glu Gln Gln Phe Lys
1               5

<210> SEQ ID NO 199
<211> LENGTH: 17
<212> TYPE: PRT
<213> ORGANISM: Arachis hypogaea

<400> SEQUENCE: 199

Arg Pro Phe Tyr Ser Asn Ala Pro Gln Glu Ile Phe Ile Gln Gln Gly
1               5                   10                  15

Arg

<210> SEQ ID NO 200
<211> LENGTH: 12
<212> TYPE: PRT
<213> ORGANISM: Arachis hypogaea

<400> SEQUENCE: 200

Ala His Val Gln Val Val Asp Ser Asn Gly Asn Arg
1               5                   10

<210> SEQ ID NO 201
<211> LENGTH: 13
<212> TYPE: PRT
<213> ORGANISM: Arachis hypogaea

<400> SEQUENCE: 201

Phe Asn Leu Ala Gly Asn His Glu Gln Glu Phe Leu Arg
1               5                   10

<210> SEQ ID NO 202
<211> LENGTH: 20
<212> TYPE: PRT
<213> ORGANISM: Arachis hypogaea

<400> SEQUENCE: 202

Asn Ala Leu Phe Val Pro His Tyr Asn Thr Asn Ala His Ser Ile Ile
1               5                   10                  15

Tyr Ala Leu Arg
            20

<210> SEQ ID NO 203
<211> LENGTH: 13
<212> TYPE: PRT
<213> ORGANISM: Arachis hypogaea

<400> SEQUENCE: 203

Ser Pro Asp Ile Tyr Asn Pro Gln Ala Gly Ser Leu Lys
1               5                   10

<210> SEQ ID NO 204
<211> LENGTH: 13
<212> TYPE: PRT
<213> ORGANISM: Arachis hypogaea

<400> SEQUENCE: 204

Trp Leu Gly Leu Ser Ala Glu Tyr Gly Asn Leu Tyr Arg
1               5                   10

<210> SEQ ID NO 205
<211> LENGTH: 23
<212> TYPE: PRT
<213> ORGANISM: Arachis hypogaea

<400> SEQUENCE: 205

Val Tyr Asp Glu Glu Leu Gln Glu Gly His Val Leu Val Val Pro Gln
1               5                   10                  15

Asn Phe Ala Val Ala Gly Lys
            20

<210> SEQ ID NO 206
<211> LENGTH: 12
<212> TYPE: PRT
<213> ORGANISM: Arachis hypogaea

<400> SEQUENCE: 206

Ser Gln Ser Glu Asn Phe Glu Tyr Val Ala Phe Lys
1               5                   10

<210> SEQ ID NO 207
<211> LENGTH: 30
<212> TYPE: PRT
<213> ORGANISM: Arachis hypogaea

<400> SEQUENCE: 207

Ala Gly Gln Glu Gln Glu Asn Glu Gly Gly Asn Ile Phe Ser Gly Phe
1               5                   10                  15

Thr Pro Glu Phe Leu Ala Gln Ala Phe Gln Val Asp Asp Arg
            20                  25                  30

<210> SEQ ID NO 208
<211> LENGTH: 15
<212> TYPE: PRT

<213> ORGANISM: Arachis hypogaea

<400> SEQUENCE: 208

Gly Glu Asn Glu Ser Asp Glu Gln Gly Ala Ile Val Thr Val Arg
1               5                   10                  15

<210> SEQ ID NO 209
<211> LENGTH: 24
<212> TYPE: PRT
<213> ORGANISM: Arachis hypogaea

<400> SEQUENCE: 209

Gln Gln Tyr Glu Arg Pro Asp Glu Glu Glu Tyr Asp Glu Asp Glu
1               5                   10                  15

Tyr Glu Tyr Asp Glu Glu Glu Arg
            20

<210> SEQ ID NO 210
<211> LENGTH: 12
<212> TYPE: PRT
<213> ORGANISM: Arachis hypogaea

<400> SEQUENCE: 210

Ser Gln Ser Asp Asn Phe Glu Tyr Val Ala Phe Lys
1               5                   10

<210> SEQ ID NO 211
<211> LENGTH: 11
<212> TYPE: PRT
<213> ORGANISM: Arachis hypogaea

<400> SEQUENCE: 211

Thr Ala Asn Asp Leu Asn Leu Leu Ile Leu Arg
1               5                   10

<210> SEQ ID NO 212
<211> LENGTH: 11
<212> TYPE: PRT
<213> ORGANISM: Arachis hypogaea

<400> SEQUENCE: 212

Thr Ala Asn Glu Leu Asn Leu Leu Ile Leu Arg
1               5                   10

<210> SEQ ID NO 213
<211> LENGTH: 33
<212> TYPE: PRT
<213> ORGANISM: Arachis hypogaea

<400> SEQUENCE: 213

Thr Asp Ser Arg Pro Ser Ile Ala Asn Leu Ala Gly Glu Asn Ser Phe
1               5                   10                  15

Ile Asp Asn Leu Pro Glu Glu Val Val Ala Asn Ser Tyr Gly Leu Pro
            20                  25                  30

Arg

<210> SEQ ID NO 214
<211> LENGTH: 12
<212> TYPE: PRT
<213> ORGANISM: Arachis hypogaea

<400> SEQUENCE: 214

Ala His Val Gln Val Val Asp Ser Asn Gly Asp Arg

<210> SEQ ID NO 215
<211> LENGTH: 12
<212> TYPE: PRT
<213> ORGANISM: Arachis hypogaea

<400> SEQUENCE: 215

Ala Gln Ser Glu Asn Tyr Glu Tyr Leu Ala Phe Lys
1               5                   10

<210> SEQ ID NO 216
<211> LENGTH: 45
<212> TYPE: PRT
<213> ORGANISM: Arachis hypogaea

<400> SEQUENCE: 216

Phe Asn Glu Gly Asp Leu Ile Ala Val Pro Thr Gly Val Ala Phe Trp
1               5                   10                  15

Leu Tyr Asn Asp His Asp Thr Asp Val Val Ala Val Ser Leu Thr Asp
            20                  25                  30

Thr Asn Asn Asn Asp Asn Gln Leu Asp Gln Phe Pro Arg
        35                  40                  45

<210> SEQ ID NO 217
<211> LENGTH: 20
<212> TYPE: PRT
<213> ORGANISM: Arachis hypogaea

<400> SEQUENCE: 217

Gly Ala Asp Glu Glu Glu Tyr Asp Glu Asp Glu Tyr Glu Tyr Asp
1               5                   10                  15

Glu Glu Asp Arg
            20

<210> SEQ ID NO 218
<211> LENGTH: 15
<212> TYPE: PRT
<213> ORGANISM: Arachis hypogaea

<400> SEQUENCE: 218

Ser Ser Asn Pro Asp Ile Tyr Asn Pro Gln Ala Gly Ser Leu Arg
1               5                   10                  15

<210> SEQ ID NO 219
<211> LENGTH: 24
<212> TYPE: PRT
<213> ORGANISM: Arachis hypogaea

<400> SEQUENCE: 219

Ser Val Asn Glu Leu Asp Leu Pro Ile Leu Gly Trp Leu Gly Leu Ser
1               5                   10                  15

Ala Gln His Gly Thr Ile Tyr Arg
            20

<210> SEQ ID NO 220
<211> LENGTH: 23
<212> TYPE: PRT
<213> ORGANISM: Arachis hypogaea

<400> SEQUENCE: 220

Val Phe Asp Glu Glu Leu Gln Glu Gly His Val Leu Val Val Pro Gln
1               5                   10                  15

```
Asn Phe Ala Val Ala Gly Lys
        20

<210> SEQ ID NO 221
<211> LENGTH: 23
<212> TYPE: PRT
<213> ORGANISM: Arachis hypogaea

<400> SEQUENCE: 221

Val Tyr Asp Glu Glu Leu Gln Glu Gly His Val Leu Val Val Pro Gln
1               5                   10                  15

Asn Phe Ala Val Ala Ala Lys
        20

<210> SEQ ID NO 222
<211> LENGTH: 30
<212> TYPE: PRT
<213> ORGANISM: Arachis hypogaea

<400> SEQUENCE: 222

Ala Gly Gln Glu Glu Glu Asn Glu Gly Gly Asn Ile Phe Ser Gly Phe
1               5                   10                  15

Thr Pro Glu Phe Leu Ala Gln Ala Phe Gln Val Asp Asp Arg
        20                  25                  30

<210> SEQ ID NO 223
<211> LENGTH: 30
<212> TYPE: PRT
<213> ORGANISM: Arachis hypogaea

<400> SEQUENCE: 223

Ala Gly Gln Glu Glu Glu Asn Glu Gly Gly Asn Ile Phe Ser Gly Phe
1               5                   10                  15

Thr Pro Glu Phe Leu Glu Gln Ala Phe Gln Val Asp Asp Arg
        20                  25                  30

<210> SEQ ID NO 224
<211> LENGTH: 11
<212> TYPE: PRT
<213> ORGANISM: Arachis hypogaea

<400> SEQUENCE: 224

Phe Phe Val Pro Pro Phe Gln Gln Ser Pro Arg
1               5                   10

<210> SEQ ID NO 225
<211> LENGTH: 30
<212> TYPE: PRT
<213> ORGANISM: Arachis hypogaea

<400> SEQUENCE: 225

Thr Asp Ser Arg Pro Ser Ile Ala Asn Leu Ala Gly Glu Asn Ser Ile
1               5                   10                  15

Ile Asp Asn Leu Pro Glu Glu Val Val Ala Asn Ser Tyr Arg
        20                  25                  30

<210> SEQ ID NO 226
<211> LENGTH: 30
<212> TYPE: PRT
<213> ORGANISM: Arachis hypogaea

<400> SEQUENCE: 226
```

```
Ala Gly Gln Glu Glu Asp Glu Gly Gly Asn Ile Phe Ser Gly Phe
1               5                   10                  15

Thr Pro Glu Phe Leu Gln Ala Phe Gln Val Asp Asp Arg
            20                  25                  30

<210> SEQ ID NO 227
<211> LENGTH: 30
<212> TYPE: PRT
<213> ORGANISM: Arachis hypogaea

<400> SEQUENCE: 227

Ala Gly Gln Glu Gln Glu Asn Glu Gly Gly Asn Ile Phe Ser Gly Phe
1               5                   10                  15

Thr Ser Glu Phe Leu Ala Gln Ala Phe Gln Val Asp Asp Arg
            20                  25                  30

<210> SEQ ID NO 228
<211> LENGTH: 15
<212> TYPE: PRT
<213> ORGANISM: Arachis hypogaea

<400> SEQUENCE: 228

Gly Glu Asn Glu Ser Glu Glu Gly Ala Ile Val Thr Val Lys
1               5                   10                  15

<210> SEQ ID NO 229
<211> LENGTH: 15
<212> TYPE: PRT
<213> ORGANISM: Arachis hypogaea

<400> SEQUENCE: 229

Gly Glu Asn Glu Ser Glu Glu Gln Gly Ala Ile Val Thr Val Lys
1               5                   10                  15

<210> SEQ ID NO 230
<211> LENGTH: 18
<212> TYPE: PRT
<213> ORGANISM: Arachis hypogaea

<400> SEQUENCE: 230

Ser Pro Asp Glu Glu Glu Tyr Asp Glu Asp Glu Tyr Ala Glu Glu
1               5                   10                  15

Glu Arg

<210> SEQ ID NO 231
<211> LENGTH: 12
<212> TYPE: PRT
<213> ORGANISM: Arachis hypogaea

<400> SEQUENCE: 231

Ser Gln Ser Glu His Phe Leu Tyr Val Ala Phe Lys
1               5                   10

<210> SEQ ID NO 232
<211> LENGTH: 33
<212> TYPE: PRT
<213> ORGANISM: Arachis hypogaea

<400> SEQUENCE: 232

Thr Asp Ser Arg Pro Ser Ile Ala Asn Leu Ala Gly Glu Asn Ser Ile
1               5                   10                  15

Ile Asp Asn Leu Pro Glu Glu Val Val Ala Asn Ser Tyr Gly Leu Pro
            20                  25                  30
```

Arg

<210> SEQ ID NO 233
<211> LENGTH: 33
<212> TYPE: PRT
<213> ORGANISM: Arachis hypogaea

<400> SEQUENCE: 233

Thr Asp Ser Arg Pro Ser Ile Ala Asn Leu Ala Gly Glu Asn Ser Val
1               5                   10                  15

Ile Asp Asn Leu Pro Glu Glu Val Val Ala Asn Ser Tyr Gly Leu Pro
            20                  25                  30

Arg

<210> SEQ ID NO 234
<211> LENGTH: 30
<212> TYPE: PRT
<213> ORGANISM: Arachis hypogaea

<400> SEQUENCE: 234

Thr Asp Ser Arg Pro Ser Ile Ala Asn Gln Ala Gly Glu Asn Ser Ile
1               5                   10                  15

Ile Asp Asn Leu Pro Glu Glu Val Val Ala Asn Ser Tyr Arg
            20                  25                  30

<210> SEQ ID NO 235
<211> LENGTH: 23
<212> TYPE: PRT
<213> ORGANISM: Arachis hypogaea

<400> SEQUENCE: 235

Val Phe Asp Glu Glu Leu Gln Glu Gly Gln Ser Leu Val Val Pro Gln
1               5                   10                  15

Asn Phe Ala Val Ala Ala Lys
            20

<210> SEQ ID NO 236
<211> LENGTH: 14
<212> TYPE: PRT
<213> ORGANISM: Arachis hypogaea

<400> SEQUENCE: 236

Ile Met Gly Glu Gln Glu Gln Tyr Asp Ser Tyr Asp Ile Arg
1               5                   10

<210> SEQ ID NO 237
<211> LENGTH: 7
<212> TYPE: PRT
<213> ORGANISM: Arachis hypogaea

<400> SEQUENCE: 237

Gln Met Val Gln Gln Phe Lys
1               5

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Asp Leu Ala Phe Pro Gly Ser Gly Glu Gln Val Glu Lys
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Thr Gly Asn Leu Glu Leu Val Ala Val Arg
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ala Gly Ser Ser Gln His Gln Glu Arg
1               5                   10

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gln Glu Gln Gln Phe Lys
1               5

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Arg Pro Phe Tyr Ser Asn Ala Pro Gln Glu Ile Phe Ile Gln Gln Gly
1               5                   10                  15

Arg

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala His Val Gln Val Val Asp Ser Asn Gly Asn Arg
1               5                   10

<210> SEQ ID NO 244
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Met Gly Glu Gln Glu Gln Tyr Asp Ser Tyr Asp Ile Arg
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Met Val Gln Gln Phe Lys
1               5

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asp Leu Ala Phe Pro Gly Ser Gly Glu Gln Val Glu Lys
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Thr Gly Asn Leu Glu Leu Val Ala Val Arg
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Ala Gly Ser Ser Gln His Gln Glu Arg
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Glu Gln Gln Phe Lys
```

```
<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Arg Pro Phe Tyr Ser Asn Ala Pro Gln Glu Ile Phe Ile Gln Gln Gly
1               5                   10                  15

Arg

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala His Val Gln Val Val Asp Ser Asn Gly Asn Arg
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Met Gly Glu Gln Glu Gln Tyr Asp Ser Tyr Asp Ile Arg
1               5                   10

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln Met Val Gln Gln Phe Lys
1               5
```

METHODS FOR CHARACTERIZING COMPOSITIONS COMPRISING PEANUT ANTIGENS

RELATED APPLICATIONS

This application is a continuation of U.S. patent application Ser. No. 16/580,638, filed Sep. 24, 2019, now U.S. Pat. No. 11,199,548, which is a division of U.S. patent application Ser. No. 15/392,233, filed Dec. 28, 2016, now U.S. Pat. No. 10,466,250, which claims the benefit of U.S. Provisional Application No. 62/272,094, filed Dec. 29, 2015, and French Patent Application No. 163306642.6, filed Dec. 8, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 10, 2021, is named 724086_SA9-180DVCON_ST25.txt and is 59,489 bytes in size.

FIELD OF THE INVENTION

The present invention relates to methods for characterizing e.g., determining release profiles, allergen signatures and the like, of therapeutic compositions comprising peanut allergens for use in treating, alleviating or otherwise reducing peanut allergy in a subject.

BACKGROUND

Peanut allergy develops when the body's immune system has an abnormal hypersensitivity response to one or more peanut allergens. Peanut allergy is one of the most common food allergies in both children and adults. It receives particular attention because it is relatively common, typically lifelong, and can cause severe allergic reactions. Peanut allergy is the leading cause of anaphylaxis and death due to food allergy. It can lead to significant burden on patients and their families. Peanut is a common food ingredient making strict avoidance difficult. Therefore, there is a relatively high rate of accidental peanut ingestion for those trying to avoid peanuts. For these reasons, peanut allergy has become an important public health issue.

Research is currently underway focused on the development of compositions for the treatment of peanut allergy. Methods are needed for determining in vitro peanut allergen release data of known and newly developed compositions, both for quality control and to predict in vivo release profiles.

SUMMARY OF THE INVENTION

The present invention is based in part on the discovery of highly sensitive methods to determine release profiles of allergens and/or to determine allergenic signatures of compositions comprising allergens. The methods described herein provide the sensitivity and accuracy needed to profile peanut allergens present in a sample, such as a protein extract, a therapeutic composition, or a dissolution or release medium and to allow measurement of low level, relevant allergens present in the sample. In exemplary embodiments, the methods include the step of detecting allergen digest products that exist in one or more isoforms of one or more allergens in the sample. The identification of allergen digest products found in multiple isoforms of a peanut allergen provides qualitative and quantitative information about a sample, which can be indicators of batch-to-batch consistency, and can provide a release profile of allergens stored on or in a substrate, such as, e.g., a nanoparticle.

In one aspect, the invention features a highly sensitive method for determining a signature of peanut allergens in a composition. The method includes the step of digesting peanut allergens present in a composition (e.g., medium or other sample) from the composition to generate allergen digest products, fragmenting the allergen digest products to generate peptide fragments, detecting and identifying the allergen digest products by mass spectrometry, and determining the signature of peanut allergens in the composition. In particular embodiments, the methods are used to determine a signature of one or more peanut allergens that are present in low concentrations in a composition. The signature includes the type and quantity (e.g., relative quantity) of allergens in the composition.

In certain embodiments, the composition is an aqueous medium, such as an aqueous pharmaceutical composition, an analytical sample, a dissolution medium or a release medium. In some embodiments, the total amount of peanut allergens in the composition is very low. For example, the amount of a particular peanut allergen (e.g., Ara h1, Ara h2, Ara h3 or Ara h6), may be less than about 2 µg/ml, less than about 1.5 µg/ml, less than about 1 µg/ml or less than about 0.5 µg/ml, e.g., about 0.2 µg/ml.

In some embodiments, the method further comprises the step of comparing a peanut allergen signature to a signature standard. The signature standard can be a peptide profile set by a regulatory authority, such as the FDA (Food and Drug Administration) or EMA (European Medicines Association), a peptide profile established by industry standards, or a profile set by expectations as determined by repeated experimentation. The signature standard can specify the types and relative amounts of peanut allergens that are expected to be found in a sample.

In certain exemplary embodiments, the allergen digest products are between about 4 amino acids and about 50 amino acids in length, between about 6 amino acids and about 30 amino acids in length, or between about 15 amino acids and about 20 amino acids in length, or are about 15, 16, 17, 18, 19 or 20 amino acids in length In certain exemplary embodiments, the steps of fragmenting the allergen digest products and detecting the peptide fragments are performed by a method that includes tandem mass spectrometry, such as Liquid Chromatography-tandem Mass Spectroscopy (LC-MS-MS), nano tandem Mass Spectroscopy (nanoLC-MS-MS) or nano High Performance Liquid Chromatography-tandem Mass Spectroscopy (nanoHPLC-MS-MS).

In certain exemplary embodiments, the signature (e.g., peanut allergen signature and/or signature standard) comprises one or more Ara h1 allergen digest products having an amino acid sequence selected from the group consisting of SEQ ID NO:17, SEQ ID NO:70, SEQ ID NO:177, SEQ ID NO:155, SEQ ID NO:93 and SEQ ID NO:40. In some embodiments, the signature comprises allergen digest products from Ara h1, Ara h2 and Ara h6. In other embodiments, the signature comprises allergen digest products from Ara h1, Ara h2, Ara h3 and Ara h6. In some embodiments, the signature includes one or more allergen digest products having amino acid sequences selected from the group consisting of SEQ ID NO:17, SEQ ID NO:70, SEQ ID NO:177, SEQ ID NO:197, SEQ ID NO:198, SEQ ID NO:199, SEQ ID NO:200, SEQ ID NO:201, SEQ ID NO:236 and SEQ ID NO:237. In some embodiments, the signature includes one or more allergen digest products having amino acid sequences selected from the group consisting of SEQ ID NO:17, SEQ ID NO:70, SEQ ID NO:197, SEQ ID NO:198, SEQ ID NO:199, SEQ ID NO:200, SEQ ID NO:201, SEQ ID NO:236 and SEQ ID NO:237.

In some embodiments, allergen digest products suitable for use in establishing a peanut allergen profile are present in more than one isoform of a peanut allergen, such as in 2, 3, 4, 5, 6, 7, 8, 10, 12, 14, 16 or more isoforms of a particular allergen (e.g., an Ara h protein or polypeptide). For example, an allergen digest product suitable for use in a peanut allergen signature profile can be present in one or any combination of in 2, 3, 4, 5, 6, 7, 8 or more of isoforms of Ara h1, in 2, 3, 4, 5, 6, 7, 8 or more of isoforms of Ara h2, in 2, 3, 4, 5, 6, 7, 8 or more of isoforms of Ara h3, and/or in 2, 3, 4, 5, 6, 7, 8 or more of isoforms of Ara h6. In some embodiments, an allergen digest product suitable for use in a peanut allergen signature profile is present in all isoforms of one or more peanut allergens.

In certain exemplary embodiments, peanut allergens are digested with one or more proteases. For example, peanut allergens may be digested with one or more proteases selected from the group consisting of trypsin, endoproteinase Lys-C and endoproteinase Arg-C.

In certain exemplary embodiments, a composition comprising peanut allergens further comprises an internal standard. For example, in some embodiments, the internal standard comprises one or more heavy isotopes, such as $^{13}C$ and/or $^{15}N$. In certain embodiments, the internal standard is not a full-length allergen, but is instead a fragment of the peptide. The fragment is typically less than 50 amino acids long (such as, e.g., between about 4 and about 50 amino acids long, between about 6 and about 30 amino acids long, or between about 10 and about 20 amino acids long). In some embodiments, the fragment has the sequence of an expected or predicted allergen digest product. In one embodiment, the internal standard is comprised of multiple peanut allergen peptides, each labeled at the C-terminus with a heavy isotope. For example, an exemplary internal standard can comprise any combination of two or more isotope-labeled fragments of an Ara h1 peptide, two or more isotope-labeled fragments of an Ara h2 peptide, two or more isotope-labeled fragments of an Ara h3 peptide and two or more isotope-labeled fragments of an Ara h6 peptide. In one embodiment, a composition comprising peanut antigens is digested with trypsin, a standard mix comprising $^{13}C$ and/or $^{15}N$-labeled peanut allergen peptides is added to the digested mix, and then the composition is assayed by fragmentation, e.g., by mass spectrometry, such as e.g., LC-MS, or LC-MS-MS.

In certain exemplary embodiments, a signature comprises allergen digest products that do not contain missed proteolytic cleavage sites.

In another aspect, the invention features a method for determining a release profile, e.g., an in vitro release profile, of a composition comprising one or more peanut allergens. In one embodiment, the method includes obtaining one or more samples from the composition at each of a plurality of time points, digesting the peanut allergens present in the one or more samples to generate allergen digest products, fragmenting the allergen digest products to generate peptide fragments, and detecting the peptide fragments for at least two of the plurality of time points to determine the release profile of the peanut allergens. The composition can be, for example, a peanut extract, a therapeutic composition comprising peanut allergens, a dissolution medium or an analytical sample. In some embodiments the composition is an aqueous medium. In some embodiments, the amount of peanut allergens in the composition is very low. For example, the amount of a particular peanut allergen (e.g., Ara h1, Ara h2, Ara h3 or Ara h6), may be less than about 2 μg/ml, less than about 1.5 μg/ml, less than about 1 μg/ml or less than about 0.5 μg/ml, e.g., about 0.2 μg/ml, or are about 15, 16, 17, 18, 19 or 20 amino acids in length. In some embodiments, allergens in a sample taken from a composition are digested to produce allergen digest products between about 4 amino acids and about 50 amino acids in length, between about 6 amino acids and about 30 amino acids in length, or between about 15 amino acids and about 20 amino acids in length. The pattern of allergen digest products obtained after digestion creates a peptide signature for the sample.

In some embodiments, the steps of fragmenting the allergen digest products and detecting the peptide fragments include one or more of a separation method and a peptide detection method. For example, in some embodiments, the steps of detecting and identifying the peptide fragments include performing methods such as LC-MS-MS, nano-LC-MS-MS, HPLC-MS-MS, or nanoHPLC-MS-MS. In some embodiments, the peptide signature includes a collection of fragments from one or more of peanut proteins Ara h1, Ara h2, Ara h3, Ara h4, Ara h5, Ara h6, Ara h7, Ara h8, Ara h9, Ara h10, Ara h11, Ara h12 and Ara h13.

In some embodiments, a peptide signature includes one or more Ara h1 allergen digest products having amino acid sequences selected from the group consisting of SEQ ID NO:17, SEQ ID NO:70, SEQ ID NO:177, SEQ ID NO:155, SEQ ID NO:93 and SEQ ID NO:40.

In some embodiments, the peptide signature comprises one or more allergen digest products from any combination of Ara h1, Ara h2 and Ara h6, or one or more allergen digest products from any combination of Ara h1, Ara h2, Ara h3 and Ara h6.

In some embodiments, the signature comprises one or more allergen digest products having amino acid sequences selected from the group consisting of SEQ ID NO:17, SEQ ID NO:70, SEQ ID NO:177, SEQ ID NO:197, SEQ ID NO:198, SEQ ID NO:199, SEQ ID NO:200, SEQ ID NO:201, SEQ ID NO:236 and SEQ ID NO:237.

In certain embodiments, allergen digest products are present in more than one isoform of a peanut allergen, such as in one, two, three, four or all isoforms of a peanut allergen, such as in one, two, three, four or all isoforms of Ara h1. In one embodiment, the allergen digest products are in more than one peanut allergen isoform.

In certain exemplary embodiments, the peanut allergens are digested with one or more proteases, such as one or more proteases selected from the group consisting of trypsin, endoproteinase Lys-C and endoproteinase Arg-C.

In certain embodiments, a sample, e.g., a sample taken from an extract or pharmaceutical composition, further comprises an internal standard. An internal standard is typically a peptide having the sequence of an expected or predicted allergen digest product, and is typically less than about 50 amino acids long (such as between about 4 and about 50 amino acids long, between about 6 and about 30 amino acids long, or between about 10 and about 20 amino acids long or about 10, about 11, about 12, about 13, about 14, about 15, about 16, about 17, about 18, about 19 or about 20 amino acids long). The internal standard can be added to the composition prior to sampling, and/or added to the sample prior to the enzymatic digestion step. In certain exemplary embodiments, the internal standard comprises one or more heavy isotopes, such as, e.g., $^{13}C$ and/or $^{15}N$.

In some embodiments, the signature comprises allergen digest products that do not contain missed (uncleaved) proteolytic cleavage sites.

In some embodiments, the composition comprises a particle that encases the allergens and/or has allergens bound to the surface. The particle can be, for example, a nanoparticle, a microparticle, a film, a capsule or a hydrogel.

In some embodiments, the release profile is obtained over a period of time, such as, e.g., over a period of hours, e.g., a three-hour period of time, a six-hour period of time, a twelve-hour period of time, or a twenty-four hour period of time.

BRIEF DESCRIPTION OF THE DRAWINGS

The foregoing and other features and advantages of the present invention will be more fully understood from the following detailed description of illustrative embodiments taken in conjunction with the accompanying drawings.

FIGS. 1A-1C depict a high quality Ara h1 peptide (SEQ ID NO:70) identified by tryptic digestion followed by MS-MS. (A) depicts the sequence, the number of uncleaved trypsin cleavage sites ("missed"), the percentage of False Discovery Rate (FDR), the number of post-translational modification sites ("PTM"), confirmation in BLAST (Basic Local Alignment Tool) that the identified sequence is unique to the target protein ("BLAST"), the database searched, and the number of isoforms in the database that included the identified sequence. (B) and (C) depict MS-MS data in Table form and graphical form, respectively.

DETAILED DESCRIPTION

Figure 1C:
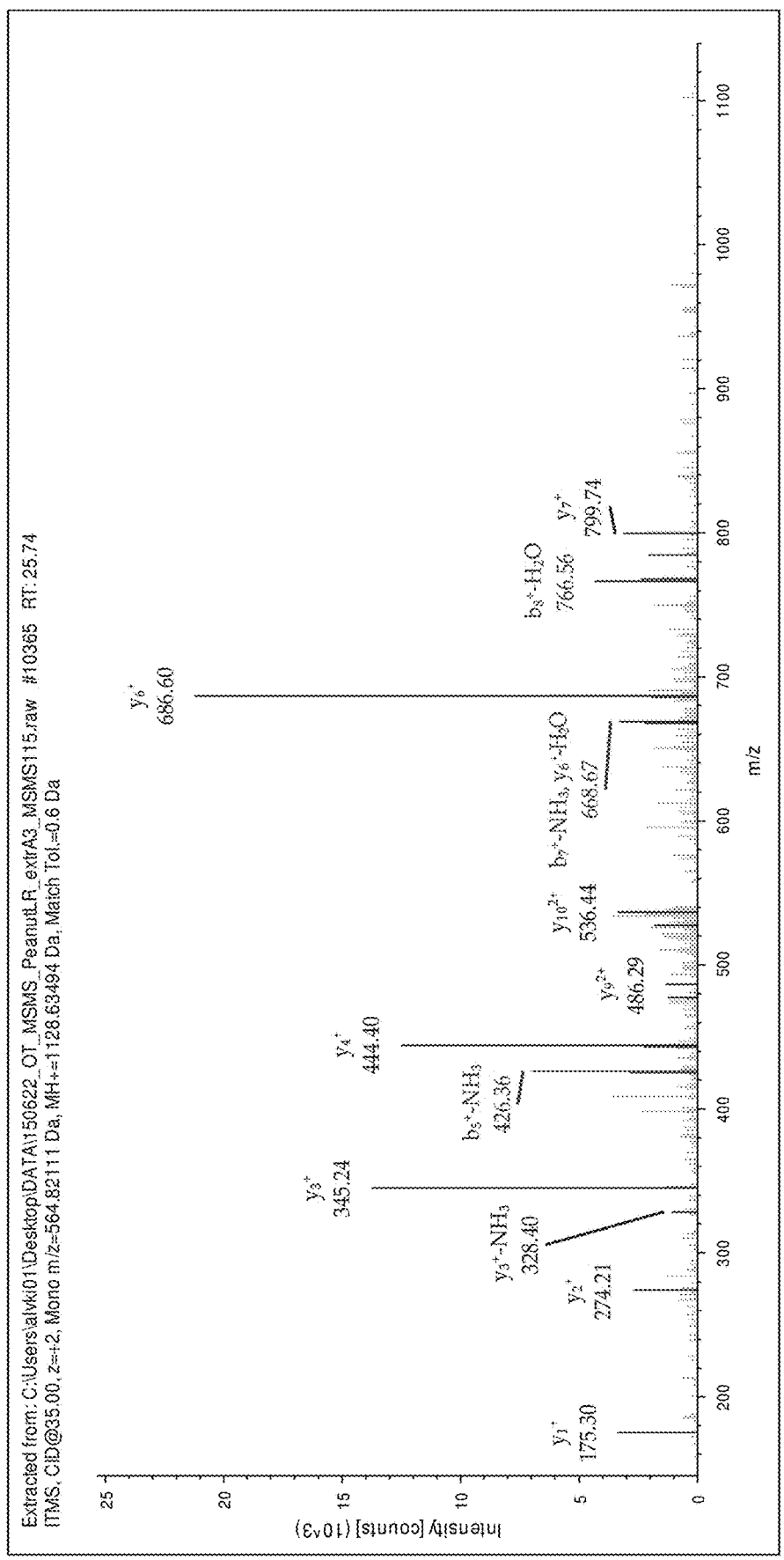

The present invention is based in part on the development of sensitive analytical methods for measuring and profiling peanut allergens present in a composition, such as an extract or a therapeutic composition, and for determining a release profile, such as an in vitro release profile, from formulated compositions comprising peanut allergens. The methods include the detection of peptides that exist in one or more isoforms of one or more allergens in a sample. The identification of peptides found in multiple isoforms of a peanut allergen provides qualitative and quantitative information about a sample, which can be indicators of batch-to-batch consistency, and can provide a release profile of antigens stored on or in a substrate, such as a nanoparticle. The methods are particularly useful for profiling allergen content in compositions containing a very low amount of peanut allergens.

As used herein, the terms "peanut," "groundnut" and "Arachis hypogea" are used interchangeably, and refer to a legume belonging to the Leguminosae family and the Papillionacea subfamily. Over 17 different peanut allergens have been identified. Peanut protein allergens include Ara h1, Ara h2, Ara h3, Ara H4, Ara h5, Ara h6, Ara h7, Ara h8, Ara h9, Ara h10, Ara h11, Ara h12, Ara h13, Ara h14, Ara h15, Ara h16 and Ara h17. GenBank Accession Numbers for the cDNA sequences of exemplary allergens include L34402.1 (Ara h1), AY007229.1 (Ara h2.0101), AY158467.1 (Ara h2.0201), AF093541.1 (Ara h3.0101), AF086821.1 (Ara h3.0201), AF059616 (Ara h5), AF092846.1 (Ara h6), AF091737.1 (Ara h7), EU046325.1 (AraH7.0201), AY328088.1 (Ara h8.0101), EF436550.1 (Ara h8.0201), EU159429.1 (Ara h9.0101), and EU161278.1 (Ara h9.0201), AY722694.2 (Ara h10.0101), AV72269.5.1 (Ara h10.0201), DQ097716.1 (Ara h11), EY396089.1 (Ara h12), EY396019.1 (AraH13), AAK13449 (Ara h14.0101), AAK13450 (Ara h14.0102), AAT11925 (Ara h14.0103), AAU21501 (Ara h15.0101), respectively (see, e.g., Leon et al., The peanut allergy epidemic: allergen molecular characterization and prospects for specific therapy. Expert Rev. Mol. Med. Vol. 9, Issue 1, January 2007; see also Arkwright et al., IgE Sensitization to the Nonspecific Lipid-Transfer Protein Ara h 9 and Peanut-Associated Bronchospasm, BioMed Research International, vol. 2013, Article ID 746507; see url address allergen.org/search.php?allergensource=Arachis+hypogaea).

In an exemplary embodiment, a signature of allergen digest products in a sample is obtained by digesting peanut allergens present in the sample to generate allergen digest products, fragmenting the allergen digest products to generate peptide fragments, and detecting and identifying the peptide fragments to obtain the signature of allergen digest products. As used herein, an "allergen digest product" refers to a peanut allergen present in an extract or sample that is digested, e.g., using an enzyme (e.g., trypsin, endoproteinase Lys-C, endoproteinase Arg-C and the like) to generate a product that is smaller than the intact allergen. The term "allergen digest product" also refers to the amino acid sequence of a peptide that would be produced if the peanut allergen were enzymatically digested.

As used herein, an "allergen" refers to a subset of antigens (e.g., peanut peptide antigens) which elicit the production of IgE in addition to other isotypes of antibodies. The terms "allergen," "natural allergen," and "wild-type allergen" may be used interchangeably.

As used herein, an "antigen" refers to a molecule (e.g., a peanut peptide) that elicits production of an antibody response (i.e., a humoral response) and/or an antigen-specific reaction with T-cells (i.e., a cellular response) in an animal.

Non-limiting examples of enzymes, specifically proteases, that are suitable to digest peanut allergens to generate allergen digest products include, but are not limited to, trypsin, endoproteinase Glu-C, endoproteinase Asp-N, chymotrypsin, endoproteinase Lys-C, and endoproteinase Arg-C, pepsin, papain, thermolysin, subtilisin, protease K, bromelain, sulfhydryl-specific protease (ficin) and the like.

As used herein, a "peptide fragment," or "gas phase peptide fragment," refers to any part or portion of the allergen that is smaller than the intact natural allergen that is generated by a fragmentation method that does not utilize an enzyme. Typically, fragmentation conditions are introduced in the gas phase, e.g., in a mass spectrometer step. In certain exemplary embodiments, a peptide fragment is less than 50 amino acids long, e.g., between about 2 and about 50 amino acids in length, between about 6 and about 30 amino acids in length, or between about 15 and about 20 amino acids in length or any values or sub-ranges within these ranges. In certain exemplary embodiments, a peptide fragment is about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, or about 49 amino acids in length.

In certain exemplary embodiments, a peptide fragment is generated by fragmenting an allergen digest product, and then using a separation process and a peptide identification method, such as Liquid Chromatography-tandem Mass Spectroscopy (LC-MS-MS), nano-LC-MS-MS, High Performance Liquid Chromatography-tandem MS (HPLC-MS-MS), nanoHPLC-MS-MS, UltraPerformance-tandem MS (UPLC-MS-MS), nanoUPLC-MS-MS, and Ultra High Performance-tandem MS (UHPLC-MS-MS), nanoUHPLC-MS-MS, or the like.

According to certain exemplary embodiments, a method described herein further comprises mass analyzing allergen digest products and/or peptide fragments using a mass analyzer. The mass analyzer typically comprises a triple quadrupole mass analyzer. According to other embodiments the mass analyzer may comprise a mass analyzer selected from the group consisting of: (i) triple quadrupole mass spectrometer, (ii) an orbitrap, such as a Fourier transform orbitrap, such as an Orbitrap ELITE™ (Thermo Scientific); (iii) a Fourier Transform ("FT") mass analyzer; (ii) a Fourier Transform Ion Cyclotron Resonance ("FTICR") mass analyzer; (iii) a Time of Flight ("TOF") mass analyzer; (iv) an orthogonal acceleration Time of Flight ("oaTOF") mass analyzer; (v) an axial acceleration time of flight mass analyzer; (vi) a magnetic sector mass spectrometer; (vii) a Paul or 3D quadrupole mass analyzer; (viii) a 2D or linear quadrupole mass analyzer; (ix) a Penning trap mass analyzer; (x) an ion trap mass analyzer; and (xiii) an electrostatic Fourier transform mass spectrometer.

In certain exemplary embodiments, the methods described herein utilize a separation process such as a chromatography method, e.g., liquid chromatography. According to an embodiment, fragmenting the allergen digest products and/or detecting and identifying the peptide fragments is performed by: (i) High Performance Liquid Chromatography ("HPLC"), (ii) anion exchange, (iii) anion exchange chromatography; (iv) cation exchange; (v) cation exchange chromatography; (vi) ion pair reversed-phase chromatography; (vii) chromatography; (viii) single dimensional electrophoresis; (ix) multi-dimensional electrophoresis; (x) size exclusion; (xi) affinity; (xii) reverse phase chromatography; (xiii) Capillary Electrophoresis Chromatography ("CEC"); (xiv) electrophoresis; (xv) ion mobility separation; (xvi) Field Asymmetric Ion Mobility Separation or Spectrometry ("FAIMS"); (xvii) capillary electrophoresis; and (xviii) supercritical fluid chromatography.

According to certain exemplary embodiments, the method further comprises ionizing allergen digest products and/or peptide fragments in a sample to be analyzed. The ion source may comprise a continuous ion source. According to an embodiment, the ion source may be selected from the group consisting of: (i) an Electrospray ionization ("ESI") ion source; (ii) a Matrix Assisted Laser Desorption Ionization ("MALDI") ion source; (iii) a Desorption Ionization on Silicon ("DIOS") ion source; and (iv) a Desorption Electrospray Ionization ("DESI") ion source.

The peanut allergen signatures described herein are generally determined by measurement of multiple reaction monitoring (MRM) transitions consisting of the peptide precursor ion, one or more fragment ions and a retention time. This measurement is performed, for example, on a triple quadrupole instrument. The signature can also be obtained by a combination of retention time and accurate high resolution mass spectrometric analysis of the intact peptide. These quantitation methods typically require a labeled internal standard and an external synthetic peptide calibration curve. In one embodiment, a signature is obtained by a nano-LC/MS/MS (nLC-MS-MS) analysis where as many peptides as possible are fragmented and identified by database analysis and nLC/MS/MS datasets consisting of retention time and mass/charge values and intensity are measured and compared to determine global proteome changes.

In certain exemplary embodiments, internal standards are used that include a combination of two or more allergen digest products from protein allergens, such as from one or more of Ara h1, Ara h2, Ara h3, Ara h4, Ara h5, Ara h6, Ara h7, Ara h8, Ara h9, Ara h10, Ara h11, Ara h12, Ara h13, Ara h14, Ara h15, Ara h16 and Ara h17. The internal standards typically have a known peptide sequence and are provided in a known quantity. In some embodiments, the internal standards include a combination of allergen digest products from the peanut allergens Ara h1, Ara h2 and Ara h6. In other embodiments, internal standards are used that include a combination of allergen digest products from Ara h1, Ara h2, Ara h3 and Ara h6. In certain exemplary embodiments, a sample can include one or more internal standards that comprise one or any combination of allergen digest products listed in Tables 19-23. In some embodiments, the standards are labeled, such with one or more heavy isotopes, e.g., $^{13}C$ or $^{15}N$.

In certain embodiments, the allergen digest products chosen to characterize the composition uniquely represent the peanut allergen or peanut allergen isoform family and are present in the majority or in all isoforms of the allergen it is derived from, enabling its usage for specific quantitation of the allergen in question, e.g., peanut allergens. Accordingly, in certain exemplary embodiments, a signature of allergen digest products is generated. As used herein, a "signature," or "allergenic signature" refers to the presence of a particular combination and amount of specific peanut allergen digest products (e.g., Ara h1, Ara h2, Ara h6 and/or Ara h3 allergen digest products). In certain exemplary embodiments, a signature comprises 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more distinct allergen digest products, each distinct product having a unique sequence.

The selection of peptides for use in a peanut allergen signature can be based on the identification of isoforms that include the peptides identified by the steps of digestion and fragmentation. A variety of sequence databases can be used to identify the sequences of peanut allergen isoforms, including UniProt (online at uniprot.org, and which includes the Swiss-Prot and TrEMBL databases), the database at Allergen Nomenclature (online at allergen.org), GenBank (online at ncbi.nlm.nih.gov), GeneCards (online at genecards.org), Ensembl (online at ensemble.org), and the like.

Any sequence alignment algorithm can be used to identify the isoforms that include the peptides identified following digestion and fragmentation of a sample comprising peanut allergens. Exemplary sequence alignment algorithms include BLAST (online at blast.ncbi.nlm.nih.gov/Blast.cgi), Clustal Omega (online at ebi.ac.uk/Tools/msa/clustalo), and the like.

The peanut allergen profiling methods can be useful for a variety of purposes. For example, the methods described herein are useful for performing batch-to-batch reproducibility assessments in peanut-containing compositions. The methods described herein are also useful for measuring the release or leakage of peanut allergens from the surface or interior of a vessel or substrate, such as from a bead or a particle (e.g., a nanoparticle or microparticle), a capsule, a film or a strip (such as, e.g., for sublingual administration of the composition), or a gel (such as a hydrogel).

In some embodiments, the peptide signature includes peptides that include one or more immunogenic epitopes, or one or more immunodominant epitopes of one or more peanut allergens. Peptide signatures that comprise immunogenic epitopes or immunodominant epitopes can provide a standard for the immunogenicity of a composition comprising peanut allergens.

As used herein, a "sample" refers to any composition containing peanut allergens. Exemplary samples include, but are not limited to, peanut-containing extracts, peanut-containing powders, analytical samples comprising one or more peanut allergens, pharmaceutical compositions (e.g., therapeutic vaccines), dissolution or release media and the like. In typical embodiments, a sample will be aqueous.

A sample for use in the allergen profiling methods featured in the invention can be a peanut extract, such as an extract made from whole roasted or raw peanuts, or from peanut flour. The extract can be for use in a pharmaceutical composition, such as for the treatment or prevention of peanut allergy. The extract can be used in a composition for oral immunotherapy (OIT), or sublingual immunotherapy (SLIT), or in a composition for use in a nanoparticle composition, with or without an adjuvant. By assessing the peanut allergen signature of the peanut extract, batch-to-batch consistencies can be monitored. The peanut allergen signature can also be used as a factor to deduce the immunogenicity of the extract, as extracts with similar signatures are expected to have similar immunogenic properties.

In some embodiments, the amount of peanut allergens in the composition is very low. For example, the amount of a particular peanut allergen (e.g., Ara h1, Ara h2, Ara h3 and/or Ara h6), may be less than about 2 µg/ml, less than about 1.5 µg/ml, less than about 1 µg/ml or less than about 0.5 µg/ml, e.g., about 0.2 µg/ml.

Peanut protein extracts can be made by methods known in the art including defatting and/or filtration methods to produce peanut allergen preparations.

A sample for use in the allergen profiling methods described herein can be a therapeutic composition, such as a liquid formulation for administration orally, sublingually, mucosally, intradermally, subcutaneously, intravenously, intramuscularly, parenterally or by inhalation.

In some embodiments, a therapeutic composition will be in the form of a film or a strip. A sample can include a piece of the film dissolved in a buffer prior to analysis by the allergen profiling methods described herein.

In other embodiments, the sample will include a substrate, such as a nanoparticle, a capsule, a film or tablet, or a gel, such as a hydrogel. The allergen profiling methods described herein are useful to assay release of peanut allergens from the substrate, such as, e.g., from a nanoparticle or capsule, or from a film or a hydrogel. The release can be from the interior of the substrate, e.g., a particle, or from the exterior (e.g., a surface) of a substrate. In one embodiment, the release profile is assayed by performing a complete release of peanut allergens and then assaying for a controlled release, such as over a period of time or in different culture or solution conditions (e.g., at different temperatures, pH or the like). The amount of allergen released in the controlled release assay is typically reported as a fraction or percentage as compared to the amount of allergen released under the complete release conditions.

In certain exemplary embodiments, two or more signatures obtained at specific points in time can be used to determine an in vitro release profile of peanut allergens in a sample containing a substrate (e.g., an aqueous sample, e.g., a dissolution or release medium). An in vitro release profile can be determined over a period of hours, days or weeks. In certain exemplary embodiments, a release profile is obtained over a period of time of about 1, 2, 3, 4, 5, 6, 7, 8, 9, 10, 11, 12, 13, 14, 15, 16, 17, 18, 19, 20, 21, 22, 23 or about 24 hours. In certain exemplary embodiments, a release profile is obtained over a period of time of about 1, 2, 3, 4, 5, 6 or about 7 days. In certain exemplary embodiments, a release profile is obtained over a period of time of about one week, about two weeks, about three weeks, about four weeks, about five weeks, about six weeks, about seven weeks, or about eight weeks. In certain exemplary embodiments, 2, 3, 4, 5, 6, 7, 8, 9, 10, 11, 12, 13, 14, 15, 20, 25, 30, 35, 40, 45, 50 or more signatures are obtained over a particular period of time. For example, the release burst of peanut allergens can be assessed within the first 24 hours in evenly spaced time points with sufficient data to determine the burst kinetics followed by the release of the remaining amount of the same allergens from the sample to help assess overall product composition performance. The release profile can include types of allergens released from the substrate and/or the relative amounts of allergen released.

In one embodiment, the methods described herein indicate release of allergen from the surface of a substrate, e.g., a nanoparticle, by detecting a burst of peptides in a dissolution or release medium near the start of the assay. If allergen is present in the interior of the substrate, the detection of allergen over time will be more gradual according to the rate of release. Allergen that is both present on the surface of a substrate and encapsulated within the substrate may be identified by an initial burst of peptide detection in the dissolution or release medium near the start of the assay, as antigen from the surface is released from the substrate, followed by a more gradual increase in peptide detection in the dissolution or release media as allergen is released (e.g., leaked) from the interior of the substrate.

As used herein, "dissolution medium," "dissolution media," "release medium" and "release media" refer to a composition that is used to provide in vitro drug release information. Dissolution or release media is useful, for example, for quality control testing of a sample for determining the release and/or stability of allergen in the sample. In choosing a suitable dissolution or release medium, it is useful to determine the analytical target profile of the allergen (e.g., delayed release, constant release, extended release and the like) and/or the allergen solubility profile. For a review of dissolution media selection, see Martin and Gray (Summer 2011) *Journal of Validation Technology.*

As used herein, "release rate" refers to the rate that an entrapped peanut allergen agent flows from a composition and into a surrounding medium in an in vitro release test. In one exemplary embodiment, the composition is first prepared for release testing by placing the composition into the appropriate in vitro release medium. This is generally performed by exchanging the buffer after centrifugation to pellet the substrate (e.g., a synthetic nanocarrier), and reconstituting of the substrate using mild conditions. In certain embodiments, the assay is started by placing the sample at 37° C. in an appropriate temperature-controlled apparatus. A sample is typically removed at various time points.

As used herein, a "release profile" refers to the types of proteins and/or peptides, e.g., peanut allergens, that are released from a substrate or vessel over time, and may also include the rate at which each particular protein, peptide and/or allergen in or on the substrate or vessel is released.

"Exhibits a pH-sensitive dissociation" refers to a coupling between two entities, such as a peanut allergen and a substrate, e.g., a carrier molecule, that is significantly reduced or eliminated by exposure of the two entities to a change in environmental pH. In certain embodiments, relevant pH-sensitive dissociations may satisfy any of the relationships or combinations thereof provided herein.

In certain exemplary embodiments, a pharmaceutical composition comprises nanocarriers and/or microcarriers, such as synthetic nanocarriers and/or synthetic microcarriers. As used herein, a "synthetic nanocarrier" or "synthetic microcarrier" refers to a discrete object that possesses at least one dimension that is less than or equal to 5 microns in size.

In some embodiments, the mass balance is compared between one or more peanut allergens in one or more compositions to be compared, such as in a sampling from a composition over a period of time across different time points, or between different batches made at different times, and/or by different methods. The comparative data can be presented as a relative quantitation, and are typically expressed as a fraction or as a percentage.

Pharmaceutical compositions containing peanut allergens can generally be formulated with carriers, excipients, and other agents that provide suitable transfer, delivery, tolerance, and the like. Exemplary formulations include, for example, powders, pastes, ointments, jellies, waxes, oils, lipids, lipid (cationic or anionic) containing vesicles (such as LIPOFECTIN™), anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J. Pharm Sci. Technol. 52:238-311.

"Pharmaceutically acceptable excipient" refers to a pharmacologically inactive substance added to a composition (e.g., a therapeutic composition) to further facilitate administration of the composition. Pharmaceutically acceptable excipients include, but are not limited to, calcium carbonate, calcium phosphate, various diluents, various sugars and types of starch, cellulose derivatives, gelatin, vegetable oils, polyethylene glycols and the like.

"Dosage form" refers to a drug (e.g., one or more peanut allergens) in a medium, carrier, vehicle or device suitable for administration to a subject.

"Effective amount" refers to that amount effective for a certain purpose. For example, when the effective amount is for a therapeutic purpose, an effective amount is an amount that treats, alleviates, ameliorates, relieves, delays onset of, inhibits progression of, reduces severity of and/or reduces incidence of one or more symptoms or features of a disease, disorder and/or condition provided herein, e.g., a peanut allergy.

"Subject" refers an animal, including mammals such as humans and non-human primates; avians; domestic household or farm animals such as cats, dogs, sheep, goats, cattle, horses and pigs; laboratory animals such as mice, rats and guinea pigs; fish; and the like.

As used herein, "vaccine" refers to a composition of matter that improves the immune response to a particular disease or disorder. A vaccine typically contains factors that stimulate a subject's immune system to recognize a specific antigen (e.g., a peanut antigen) as foreign and eliminate it from the subject's body. A vaccine also establishes an immunologic "memory" such the antigen will be quickly recognized and responded to if a subject is re-challenged. Vaccines can be prophylactic (for example to prevent future infection by any pathogen) or therapeutic (for example a vaccine against a peanut antigen for the treatment of peanut allergy).

"Administering" or "administration" means providing a drug to a subject in a manner that is pharmacologically useful.

As used herein, an "epitope" refers to a binding site including an amino acid motif of between approximately six and fifteen amino acids which can be bound by an immunoglobulin (e.g., IgE, IgG, etc.) or recognized by a T-cell receptor when presented by an APC in conjunction with the major histocompatibility complex (WIC). A linear epitope is one where the amino acids are recognized in the context of a simple linear sequence. A conformational epitope is one where the amino acids are recognized in the context of a particular three dimensional structure. The peanut allergen signatures identified by the methods featured in the invention may comprise one or more peanut epitopes. An immunogenic epitope can provoke an immune response in the body, e.g., an allergic response.

As used herein, an "immunodominant epitope" refers to an epitope which is bound by antibody in a large percentage of the sensitized population or where the titer of the antibody is high, relative to the percentage or titer of antibody reaction to other epitopes present in the same antigen. In one embodiment, an immunodominant epitope is bound by antibody in more than 50% of the sensitive population, more preferably more than 60%, 70%, 80%, 90%, 95%, or 99% of the sensitive population. The peanut allergen signatures identified by the methods featured in the invention will typically comprising one or more peanut immunodominant epitopes.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

Example I

Peanut Allergen Signature

The development and initial preliminary validation of a method for the relative quantitation of four peanut allergens, Ara h1, Ara h2, Ara h3 and Ara h6, are described below. The method utilized liquid chromatography coupled to tandem mass spectrometry, and was based on the measurement of representative tryptic peptides derived from each of these proteins. The peptides were chosen in each case to include the majority of the reported allergenic protein isoforms.

The profiling method was dependent on the digest reproducibility and digest efficiency for the protein of interest in a complex protein mixture. Not all proteolytic peptides are good candidates for quantitation, and whereas good ionization efficiency and consistent tryptic cleavage, as well as low probability of the peptide harboring post-translational modification, are important aspects of the selection process, issues such as interference from other peptides and other matrix effects in a complex digest, are more difficult to predict. Once selected, a series of both heavy isotope labeled peptides and non-labeled synthetic versions of the selected peptides were procured and used as internal standards and for buffer calibration curves, respectively.

Peanut extracts prepared from lightly roasted peanut flour (Golden Peanut and Tree Nuts, Alpharetta, GA) were digested in quadruplicate with trypsin, and then a standard was added to the digested sample. The standard contained two Ara h1 peptides, two Ara h2 peptides, two Ara h3 peptides, and two Ara h6 peptides. The peptides in the internal standard were labeled with one or both of $^{13}$C and $^{15}$N. The sequences of the internal standards are provided in Tables 1 and 2 below.

TABLE 1

Unlabeled synthetic "Light" peptides for internal standard

| Peptide sequence | peptide | formula |
|---|---|---|
| DLAFPGSGEQVEK (SEQ ID NO: 238) | ARA_L1-1 | C60 H93 N15 O22 |
| GTGNLELVAVR (SEQ ID NO: 239) | ARA_L1-2 | C48 H85 N15 O16 |
| GAGSSQHQER (SEQ ID NO: 240) | ARA_L2-1 | C40 H65 N17 O17 |
| QQEQQFK (SEQ ID NO: 241) | ARA_L2-2 | C40 H62 N12 O14 |
| RPFYSNAPQEIFIQQGR (SEQ ID NO: 242) | ARA_L3-1 | C93 H139 N27 O26 |
| AHVQVVDSNGNR (SEQ ID NO: 243) | ARA_L3-2 | C52 H86 N20 O19 |
| IMGEQEQYDSYDIR (SEQ ID NO: 244) | ARA_L6-1 | C74 H111 N19 O28 S1 |
| QMVQQFK (SEQ ID NO: 245) | ARA_L6-2 | C40 H65 N11 O11 S1 |

TABLE 2

Labeled synthetic "Heavy" peptides for internal standard

| Peptide sequence | peptide | formula |
|---|---|---|
| DLAFPGSGEQVEK* (SEQ ID NO: 246) | ARA_H1-1 | 13C6 C54 H93 15N2 N13 O22 |
| GTGNLELVAVR* (SEQ ID NO: 247) | ARA_H1-2 | 13C6 C42 H85 15N4 N11 O16 |
| GAGSSQHQER* (SEQ ID NO: 248) | ARA_H2-1 | 13C6 C34 H65 15N4 N13 O17 |
| QQEQQFK* (SEQ ID NO: 249) | ARA_H2-2 | 13C6 C34 H62 15N2 N10 O14 |
| RPFYSNAPQEIFIQQGR* (SEQ ID NO: 250) | ARA_H3-1 | 13C6 C87 H139 15N4 N23 O26 |
| AHVQVVDSNGNR* (SEQ ID NO: 251) | ARA_H3-2 | 13C6 C46 H86 15N4 N16 O19 |
| IMGEQEQYDSYDIR* (SEQ ID NO: 252) | ARA_H6-1 | 13C6 C68 H111 15N4 N14 O28 S1 |
| QMVQQFK* (SEQ ID NO: 253) | ARA_H6-2 | 13C6 C34 H65 15N4 N7 O11 S1 |

K* and R* are heavy isotope labeled amino acids where the carbon-12 has been replaced with carbon-13 and nitrogen-14 with nitrogen-15 resulting in 13C6 15N2 for lysine and 13C6 15N4 for arginine Notably, additional peptides could have been selected and the particular characteristics of the proteins made it difficult to fulfill all desirable features for all peptides. For example, the two peptides for Ara h6 contain methionine, which is undesirable but difficult to avoid as Ara h6 contains an unusually high content of S-containing amino acids. Similarly, Ara h3 contains N-terminal "missed" cleavage sites that have been found to be stable. Often, tryptic cleavage sites that are very close to each other will result in preferential cleavage of one of the sites, not both.

The internal standards were used to quantitate the digested products. Buffer calibration curves of synthetic unlabeled signature peptides were generated with heavy isotope-labeled internal standards added to both the peanut extract digest and the calibration curve. Relative quantification was performed applying the internal standard and calibration curve to determine the relative amount of signature peptides in the peanut extract digest.

The samples containing the digested test allergens and the standards were analyzed by nanoHPLC-MS-MS gas phase fragmentation (Orbitrap ThermoScientific). Using the top-15 method, one sample (out of the four total) was analyzed three times, and the remaining three samples were analyzed one time, to generate a total of six data files. These data files were analyzed by Proteome Discoverer™ Software (Thermo Scientific). Applying the top-15 method to identify the most abundant proteins assured that peptides of high ionization and fragmentation efficiency would be identified in a consistent manner across the data sets.

The identities of the resulting fragments were determined using the UniProt sequence database at uniprot.org.

Over 90% of all known peanut allergens were detected from the peanut flour sample, including Ara h1, Ara h2, Ara h3, Ara h5, Ara h6, Ara h7, Ara h8, Ara h10, Ara h11, Ara h14, Ara h15, and Ara h Agglutinin. A survey of the identified allergens is illustrated in Tables 3-18 below.

Ara h1, Ara h2, Ara h3 and Ara h6 represent the major peanut allergens.

TABLE 3

Ara h1 isoforms detected in peanut flour.

| Peanut Allergen | UniProt Ref | Peak Identified by nanoHPLC-MS-MS |
|---|---|---|
| Ara h 1 | B3IXL2 | No |
| Ara h 1 | E5G076 | Yes |
| Ara h 1 | N1NEW2 | No |
| Ara h 1 | N1NG13 | No |
| Ara h 1 | P43237 | Yes |
| Ara h 1 | Q6PSU3 | Yes |
| Ara h 1 | Q6PSU4 | Yes |
| Ara h 1 | Q6PSU5 | Yes |
| Ara h 1 | Q6PSU6 | Yes |
| Ara h 1.0101 | P43238 | Yes |

TABLE 4

Ara h2 isoforms detected in peanut flour.

| Peanut Allergen | UniProt Ref | Peak Identified by nanoHPLC-MS-MS |
|---|---|---|
| Ara h 2 | C0LJJ1 | No |
| Ara h 2.0101 | Q6PSU2 | Yes |
| Ara h 2.0201 | Q6PSU2 | Yes |

TABLE 5

Ara h3 isoforms detected in peanut flour

| Peanut Allergen | UniProt Ref | Peak Identified by nanoHPLC-MS-MS |
|---|---|---|
| Ara h 3 | A1DZF0 | Yes |
| Ara h 3 | A1DZF1 | Yes |
| Ara h 3 | B5TYU1 | Yes |
| Ara h 3 | E5G077 | Yes |
| Ara h 3 | Q0GM57 | Yes |
| Ara h 3 | Q5I6T2 | Yes |
| Ara h 3 | Q647H2 | Yes |
| Ara h 3 | Q647H3 | Yes |
| Ara h 3 | Q647H4 | Yes |
| Ara h 3 | Q6IWG5 | Yes |
| Ara h 3 | Q6T2T4 | Yes |
| Ara h 3 | Q8LKN1 | Yes |
| Ara h 3 | Q8LL03 | Yes |
| Ara h 3 | Q9FZ11 | Yes |
| Ara h 3.0101 | O82580 | Yes |
| Ara h 3.0201 | Q9SQH7 | Yes |
| n/a | O82580 | Yes |
| n/a | Q9SQH7 | Yes |

TABLE 6

Ara h5 isoforms identified in peanut flour

| Peanut Allergen | UniProt Ref | Peak Identified by nanoHPLC-MS-MS |
|---|---|---|
| Ara h 5 | D3K177 | Yes |
| Ara h 5 | L7QH52 | Yes |
| Ara h 5 | Q5XXQ5 | Yes |
| Ara h 5.0101 | Q9SQI9 | Yes |

TABLE 7

Ara h6 isoforms identified in peanut flour

| Peanut Allergen | UniProt Ref | Peak Identified by nanoHPLC-MS-MS |
|---|---|---|
| Ara h 6 | A1DZE9 | Yes |
| Ara h 6 | A5Z1R0 | No |
| Ara h 6.0101 | Q647G9 | Yes |

TABLE 8

Ara h7 isoforms identified in peanut flour

| Peanut Allergen | UniProt Ref | Peak Identified by nanoHPLC-MS-MS |
|---|---|---|
| Ara h 7 | Q647G8 | Yes |
| Ara h 7.0101 | Q9SQH1 | Yes |
| Ara h 7.0201 | B4XID4 | Yes |

TABLE 9

Ara h8 isoforms identified in peanut flour

| Peanut Allergen | UniProt Ref | Peak Identified by nanoHPLC-MS-MS |
|---|---|---|
| Ara h 8 | B1PYZ4 | Yes |
| Ara h 8 | B2ZGS2 | Yes |
| Ara h 8 | Q0PKR4 | Yes |
| Ara h 8 | Q2YHR1 | Yes |

TABLE 9-continued

Ara h8 isoforms identified in peanut flour

| Peanut Allergen | UniProt Ref | Peak Identified by nanoHPLC-MS-MS |
|---|---|---|
| Ara h 8.0101 | Q6VT83 | Yes |
| Ara h 8.0201 | B0YIU5 | Yes |

TABLE 10

Ara h9 isoforms identified in peanut flour

| Peanut Allergen | UniProt Ref | Peak Identified by nanoHPLC-MS-MS |
|---|---|---|
| Ara h 9.0101 | B6CEX8 | Yes |
| Ara h 9.0201 | B6CG41 | Yes |

TABLE 11

Ara h10 isoforms identified in peanut flour.

| Peanut Allergen | UniProt Ref | Peak Identified by nanoHPLC-MS-MS |
|---|---|---|
| Ara h 10.0101 | Q647G5 | Yes |
| Ara h 10.0102 | Q647G4 | Yes |

TABLE 12

Ara h11 isoforms identified in peanut flour.

| Peanut Allergen | UniProt Ref | Peak Identified by nanoHPLC-MS-MS |
|---|---|---|
| Ara h 11.0101 | Q45W87 | Yes |
| Ara h 11.0102 | Q45W86 | Yes |

TABLE 13

Ara h12 isoforms identified in peanut flour.

| Peanut Allergen | UniProt Ref | Peak Identified by nanoHPLC-MS-MS |
|---|---|---|
| Ara h 12.0101 | EY396089 | No |

TABLE 14

Ara h13 isoforms identified in peanut flour.

| Peanut Allergen | UniProt Ref | Peak Identified by nanoHPLC-MS-MS |
|---|---|---|
| Ara h 13.0101 | EY396019 | No |

TABLE 15

Ara h14 isoforms identified in peanut flour.

| Peanut Allergen | UniProt Ref | Peak Identified by nanoHPLC-MS-MS |
|---|---|---|
| Ara h 14.0101 | Q9AXI1 | Yes |
| Ara h 14.0102 | Q9AXI0 | Yes |
| Ara h 14.0103 | Q6J1J8 | Yes |

TABLE 16

Ara h15 isoforms identified in peanut flour.

| Peanut Allergen | UniProt Ref | Peak Identified by nanoHPLC-MS-MS |
|---|---|---|
| Ara h 15.0101 | Q647G3 | Yes |

TABLE 17

Ara h Agglutinin isoforms identified in peanut flour.

| Peanut Allergen | UniProt Ref | Peak Identified by nanoHPLC-MS-MS |
|---|---|---|
| Ara h Agglutinin | P02872 | Yes |
| Ara h Agglutinin | Q38711 | Yes |
| Ara h Agglutinin | Q43373 | Yes |
| Ara h Agglutinin | Q43375 | Yes |
| Ara h Agglutinin | Q8W0P8 | Yes |

TABLE 18

Ara h hypothetical isoforms identified in peanut flour.

| Hypothetical Peanut Allergen | UniProt Ref | Peak Identified by nanoHPLC-MS-MS |
|---|---|---|
| Ara i 2 | A5Z1Q9 | No |
| Ara i 6 | A5Z1Q6 | No |
| Ara d 2 | A5Z1Q8 | No |
| Ara d 2 | A8VT41 | No |
| Ara d 2 | A8VT44 | No |
| Ara d 2 | A8VT45 | No |
| Ara d 2 | A8VT50 | No |
| Ara d 6 | A5Z1Q5 | No |

Peptides of the major allergens are identified to form a collection of peptides for use as an indicator of peanut allergen content in a composition (e.g., a "peanut peptide signature"). An ideal peptide signature utilizes peptides that represent completely cleaved true tryptic digest products (with the possible exception of peptides that contain sequential arginine and/or lysine residues), where one or the other cleavage site is typically preferentially cleaved. Selected peptides also typically have sequence conservation with a False Discovery Rate (FDR) of less than 1%, and sequence conservation across multiple isoforms. Further, selected peptides typically have no or minimal post-translational modifications, including oxidation and glycosylation, and have high detection quality based on manual curation of tandem mass spectrometry (MS-MS). Isoforms are represented by genetic variations, including peptides generated by truncated or deleted sequences. An example of a high quality peptide as identified by MS-MS is the Ara h1 peptide illustrated in FIGS. 1A to 1C.

For example, Ara h1k heterogeneity was determined by comparing sequence variations in the UniProt database records. Exemplary Ara h1 allergen digest products identified from UniProt reference P43238 are shown in Table 19. Sequences from other UniProt Ara h1 records were also compared (see Table 20). Preferred Ara h1 allergen digest products were selected as being useful in a peanut allergen signature based on: 1) preferentially zero missed tryptic cleavage sites; 2) presence in all sequences with a False Discovery Rate (FDR) of less than 1%; 3) no or minimal post-translational modification sites; 4) high quality fragments as determined by manual curation of tandem Mass Spectroscopy (MS-MS) data; 5) an indication by BLAST search that the sequence is unique within the peanut proteome; and 6) presence of the sequence a maximum number of isoforms. The resulting initial list of allergen digest products that were determined to be most useful candidates for profiling peanut antigens in the peanut flour extract are shown in Tables 20-23, representing peanut allergens from Ara h1, Ara h2, Ara h3 and Ara h6, respectively.

TABLE 19

Ara h1 allergen digest products from UniProt Ref. P43238.

| Ara h1 Peptide Sequence | SEQ ID NO: |
|---|---|
| ACESRCTKLEYDPR | 1 |
| ACESRCTKLEYDPRCVYDPR | 2 |
| AMVIVVVNK | 3 |
| AMVIVVVNKGTGNLELVAVR | 4 |
| AMVIVVVNKGTGNLELVAVRK | 5 |
| CLQSCQQEPDDLK | 6 |
| CLQSCQQEPDDLKQK | 7 |
| CLQSCQQEPDDLKQKACESR | 8 |
| CLQSCQQEPDDLKQKACESRCTK | 9 |
| CTKLEYDPR | 10 |
| CTKLEYDPRCVYDPR | 11 |
| CTKLEYDPRCVYDPRGHTGTTNQR | 12 |
| CVYDPR | 13 |
| CVYDPRGHTGTTNQR | 14 |
| CVYDPRGHTGTTNQRSPPGER | 15 |
| CVYDPRGHTGTTNQRSPPGERTR | 16 |
| DLAFPGSGEQVEK | 17 |
| DLAFPGSGEQVEKLIK | 18 |
| DNVIDQIEKQAK | 19 |
| DQSSYLQGFSR | 20 |
| DQSSYLQGFSRNTLEAAFNAEFNEIRR | 21 |
| EDQEEENQGGKGPLLSILK | 22 |
| EDWRRPSHQQPR | 23 |
| EEDWRQPREDWR | 24 |
| EEDWRQPREDWRRPSHQQPR | 25 |
| EEEEDEDEEEEGSNREVRRYTAR | 26 |
| EEGGRWGPAGPR | 27 |
| EEGGRWGPAGPRER | 28 |
| EEGGRWGPAGPRERER | 29 |
| EETSRNNPFYFPSR | 30 |
| EETSRNNPFYFPSRR | 31 |
| EETSRNNPFYFPSRRFSTR | 32 |

TABLE 19-continued

Ara h1 allergen digest products from UniProt Ref. P43238.

| Ara h1 Peptide Sequence | SEQ ID NO: |
|---|---|
| EGALMLPHFNSK | 33 |
| EGALMLPHFNSKAMVIVVVNK | 34 |
| EGDVFIMPAAHPVAINASSELHLLGFGINAENNHRIFLAGDK | 35 |
| EGDVFIMPAAHPVAINASSELHLLGFGINAENNHRIFLAGDKDNVIDQIEK | 36 |
| EGEPDLSNNFGK | 37 |
| EGEPDLSNNFGKLFEVKPDKK | 38 |
| EGEPDLSNNFGKLFEVKPDKKNPQLQDLDMMLTCVEIK | 39 |
| EGEQEWGTPGSHVR | 40 |
| EGEQEWGTPGSHVREETSRNNPFYFPSRR | 41 |
| EHVEELTK | 42 |
| EHVEELTKHAK | 43 |
| EQQQRGRR | 44 |
| EQQQRGRREEEEDEDEEEEGSNR | 45 |
| EREEDWR | 46 |
| EREEDWRQPR | 47 |
| EREREEDWR | 48 |
| EREREEDWRQPR | 49 |
| ESHFVSARPQSQSQSPSSPEK | 50 |
| ESHFVSARPQSQSQSPSSPEKESPEKEDQEEENQGGK | 51 |
| ESPEKEDQEEENQGGK | 52 |
| EVRRYTAR | 53 |
| FDQRSR | 54 |
| FDQRSRQFQNLQNHR | 55 |
| FSTRYGNQNGR | 56 |
| FSTRYGNQNGRIR | 57 |
| FSTRYGNQNGRIR | 58 |
| GHTGTTNQRSPPGERTR | 59 |
| GHTGTTNQRSPPGERTRGR | 60 |
| GQRRWSTR | 61 |
| GRQPGDYDDDR | 62 |
| GRQPGDYDDDRR | 63 |
| GRQPGDYDDDRRQPR | 64 |
| GRQPGDYDDDRRQPR | 65 |
| GRREEEEDEDEEEEGSNR | 66 |
| GRREEEEDEDEEEEGSNREVR | 67 |
| GSEEEGDITNPINLR | 68 |
| GSEEEGDITNPINLREGEPDLSNNFGK | 69 |
| GTGNLELVAVR | 70 |
| GTGNLELVAVRK | 71 |
| HADADNILVIQQGQATVTVANGNNR | 72 |
| HADADNILVIQQGQATVTVANGNNRK | 73 |
| HADADNILVIQQGQATVTVANGNNRKSFNLDEGHALR | 74 |
| HAKSVSKK | 75 |
| HAKSVSKKGSEEEGDITNPINLR | 76 |
| HDNQNLR | 77 |
| HDNQNLRVAKISMPVNTPGQFEDFFPASSR | 78 |
| IFLAGDKDNVIDQIEK | 79 |
| IFLAGDKDNVIDQIEKQAK | 80 |
| IFLAGDKDNVIDQIEKQAKDLAFPGSGEQVEK | 81 |
| IPSGFISYILNR | 82 |
| IPSGFISYILNRHDNQNLR | 83 |
| IPSGFISYILNRHDNQNLRVAK | 84 |
| IPSGFISYILNRHDNQNLRVAKISMPVNTPGQFEDFFPASSR | 85 |
| IRPEGREGEQEWGTPGSHVREETSR | 86 |
| IRPEGREGEQEWGTPGSHVREETSRNNPFYFPSR | 87 |
| IRVLQRFDQR | 88 |
| ISMPVNTPGQFEDFFPASSR | 89 |
| ISMPVNTPGQFEDFFPASSRDQSSYLQGFSR | 90 |
| ISMPVNTPGQFEDFFPASSRDQSSYLQGFSRNTLEAAFNAEFNEIR | 91 |
| ISMPVNTPGQFEDFFPASSRDQSSYLQGFSRNTLEAAFNAEFNEIRR | 92 |
| IVQIEAKPNTLVLPK | 93 |
| KEQQQR | 94 |
| KEQQQRGRR | 95 |
| KGSEEEGDITNPINLR | 96 |
| KGSEEEGDITNPINLREGEPDLSNNFGK | 97 |
| KGSEEEGDITNPINLREGEPDLSNNFGKLFEVKPDK | 98 |
| KIRPEGREGEQEWGTPGSHVREETSR | 99 |
| KNPQLQDLDMMLTCVEIK | 100 |
| KNPQLQDLDMMLTCVEIKEGALMLPHFNSK | 101 |
| KNPQLQDLDMMLTCVEIKEGALMLPHFNSKAMVIVVVNK | 102 |
| KSFNLDEGHALR | 103 |

TABLE 19-continued

Ara h1 allergen digest products from UniProt Ref. P43238.

| Ara h1 Peptide Sequence | SEQ ID NO: |
|---|---|
| KSFNLDEGHALRIPSGFISYILNR | 104 |
| KSFNLDEGHALRIPSGFISYILNRHDNQNLR | 105 |
| KTENPCAQR | 106 |
| KTENPCAQRCLQSCQQEPDDLK | 107 |
| KTENPCAQRCLQSCQQEPDDLKQK | 108 |
| LEYDPR | 109 |
| LEYDPRCVYDPR | 110 |
| LEYDPRCVYDPRGHTGTTNQR | 111 |
| LEYDPRCVYDPRGHTGTTNQRSPPGER | 112 |
| LFEVKPDK | 113 |
| LFEVKPDKK | 114 |
| LFEVKPDKKNPQLQDLDMMLTCVEIK | 115 |
| LFEVKPDKKNPQLQDLDMMLTCVEIKEGALMLPHFNSK | 116 |
| LIKNQKESHFVSARPQSQSQSPSSPEK | 117 |
| NNPFYFPSR | 118 |
| NNPFYFPSRR | 119 |
| NNPFYFPSRRFSTR | 120 |
| NNPFYFPSRRFSTRYGNQNGR | 121 |
| NPQLQDLDMMLTCVEIK | 122 |
| NPQLQDLDMMLTCVEIKEGALMLPHFNSK | 123 |
| NPQLQDLDMMLTCVEIKEGALMLPHFNSKAMVIVVVNK | 124 |
| NQKESHFVSARPQSQSQSPSSPEK | 125 |
| NQKESHFVSARPQSQSQSPSSPEKESPEKEDQEEENQGGK | 126 |
| NTLEAAFNAEFNEIR | 127 |
| NTLEAAFNAEFNEIRR | 128 |
| NTLEAAFNAEFNEIRRVLLEENAGGEQEER | 129 |
| NTLEAAFNAEFNEIRRVLLEENAGGEQEERGQR | 130 |
| QAKDLAFPGSGEQVEK | 131 |
| QFQNLQNHR | 132 |
| QFQNLQNHRIVQIEAKPNTLVLPKHADADNILVIQQGQATVTVANGNNRK | 133 |
| QKACESR | 134 |
| QKACESRCTKLEYDPR | 135 |
| QPGDYDDDRR | 136 |
| QPGDYDDDRRQPR | 137 |
| QPGDYDDDRRQPRR | 138 |
| QPREDWRRPSHQQPR | 139 |
| QPREDWRRPSHQQPRK | 140 |
| QPRREEGGR | 141 |
| QPRREEGGRWGPAGPR | 142 |
| REEEEDEDEEEEGSNR | 143 |
| REEEEDEDEEEEGSNREVR | 144 |
| REEEEDEDEEEEGSNREVRR | 145 |
| REEGGR | 146 |
| REEGGRWGPAGPR | 147 |
| REEGGRWGPAGPRER | 148 |
| RFSTRYGNQNGR | 149 |
| RFSTRYGNQNGRIR | 150 |
| RPSHQQPR | 151 |
| RVLLEENAGGEQEER | 152 |
| RVLLEENAGGEQEERGQR | 153 |
| RWSTRSSENNEGVIVK | 154 |
| SFNLDEGHALR | 155 |
| SFNLDEGHALRIPSGFISYILNR | 156 |
| SFNLDEGHALRIPSGFISYILNRHDNQNLR | 157 |
| SPPGERTRGR | 158 |
| SPPGERTRGRQPGDYDDDR | 159 |
| SRQFQNLQNHR | 160 |
| SRQFQNLQNHRIVQIEAKPNTLVLPKHADADNILVIQQGQATVTVANGNNR | 161 |
| SSENNEGVIVK | 162 |
| SSENNEGVIVKVSK | 164 |
| SSENNEGVIVKVSKEHVEELTK | 164 |
| SSPYQKK | 165 |
| SSPYQKKTENPCAQR | 166 |
| SSPYQKKTENPCAQRCLQSCQQEPDDLK | 167 |
| SVSKKGSEEEGDITNPINLR | 168 |
| TENPCAQR | 169 |
| TENPCAQRCLQSCQQEPDDLK | 170 |
| TENPCAQRCLQSCQQEPDDLKQK | 171 |
| TENPCAQRCLQSCQQEPDDLKQKACESR | 172 |
| TRGRQPGDYDDDR | 173 |
| TRGRQPGDYDDDRR | 174 |
| VAKISMPVNTPGQFEDFFPASSR | 175 |

TABLE 19-continued

Ara h1 allergen digest products from UniProt Ref. P43238.

| Ara h1 Peptide Sequence | SEQ ID NO: |
|---|---|
| VAKISMPVNTPGQFEDFFPASSRDQSSYLQGFSRNTLEAAFNAEFNEIR | 176 |
| VLLEENAGGEQEER | 177 |
| VLLEENAGGEQEERGQR | 178 |
| VLLEENAGGEQEERGQRR | 179 |
| VLLEENAGGEQEERGQRRWSTR | 180 |
| VLQRFDQRSRQFQNLQNHR | 181 |
| VSKEHVEELTK | 182 |
| VSPLMLLLGILVLASVSATHAK | 183 |
| WGPAGPR | 184 |
| WGPAGPRER | 185 |
| WGPAGPRERER | 186 |
| WSTRSSENNEGVIVK | 187 |
| WSTRSSENNEGVIVKVSKEHVEELTK | 188 |
| YGNQNGR | 189 |
| YGNQNGRIRVLQR | 190 |
| YGNQNGRIRVLQRFDQR | 191 |
| YTARLKEGDVFIMPAAHPVAINASSELHLLGFGINAENNHRIFLAGDK | 192 |

TABLE 20

Ara h1 Sequences Identified in Prepared Peanut Extract

| Ara h1 Peptide Sequence | # Appearance in 7 UniProt References | UniProt Reference Nos |
|---|---|---|
| DLAFPGSGEQVEK (SEQ ID NO: 17) | 7 | P43238, P43237, E5G076, Q6PSU3, Q6PSU6, Q6PSU5, Q6PSU4 |
| GTGNLELVAVR (SEQ ID NO: 70) | 7 | P43238, P43237, E5G076, Q6PSU3, Q6PSU6, Q6PSU5, Q6PSU4 |
| VLLEENAGGEQEER (SEQ ID NO: 177) | 7 | P43238, P43237, E5G076, Q6PSU3, Q6PSU6, Q6PSU5, Q6PSU4 |
| DQSSYLQGFSR (SEQ ID NO: 20) | 5 | P43238, P43237, E5G076, Q6PSU3, Q6PSU4 |
| HADADNILVIQQGQATVTVANGNNR (SEQ ID NO: 72) | 5 | P43238, P43237, E5G076, Q6PSU3, Q6PSU4 |
| NTLEAAFNAEFNEIR (SEQ ID NO: 127) | 5 | P43238, P43237, E5G076, Q6PSU3, Q6PSU4 |
| EQEWEEEEEDEEEEGSNR (SEQ ID NO: 193) | 4 | P43237, E5G076, Q6PSU3, Q6PSU6 |
| IPSGFISYILNR (SEQ ID NO: 82) | 4 | P43238, P43237, Q6PSU3, Q6PSU4 |
| NNPFYFPSR (SEQ ID NO: 118) | 4 | P43238, P43237, E5G076, Q6PSU3 |
| SFNLDEGHALR (SEQ ID NO: 155) | 4 | P43238, P43237, Q6PSU3, Q6PSU4 |
| GSEEEDITNPINLR (SEQ ID NO: 194) | 3 | P43237, Q6PSU3, Q6PSU6 |
| IVQIEAKPNTLVLPK (SEQ ID NO: 93) | 3 | P43238, E5G076, Q6PSU4 |
| EGEQEWGTPGSEVR (SEQ ID NO: 195) | 2 | P43237, Q6PSU3 |
| EGEQEWGTPGSHVR (SEQ ID NO: 40) | 2 | P43238, E5G076 |
| IVQIEARPNTLVLPK (SEQ ID NO: 196) | 2 | P43237, Q6PSU3 |

TABLE 21

Ara h2 Sequences Identified in Prepared Peanut Extract

| Ara h2 Peptide Sequence | # Appearance in 1 UniProt References | UniProt Reference Nos |
|---|---|---|
| GAGSSQHQER (SEQ ID NO: 197) | 1 | Q6PSU2 |
| QQEQQFK (SEQ ID NO: 198) | 1 | Q6PSU2 |

TABLE 22

Ara h3 Sequences Identified in Prepared Peanut Extract

| Ara h3 Peptide Sequence | # Appearance in 16 UniProt References | UniProt Reference Nos |
|---|---|---|
| RPFYSNAPQEIFIQQGR (SEQ ID NO: 199) | 12 | Q5I6T2, B5TYU1, Q9FZ11, A1DZF1, Q82580, Q8LL03, Q9SQH7, Q647H4, Q6T2T4, Q8LKN1, Q647H3, A1DZF0 |
| AHVQVVDSNGNR (SEQ ID NO: 200) | 10 | Q5I6T2, B5TYU1, Q9FZ11, O82580, Q0GM57, E5G077, Q9SQH7, Q647H3, Q6IWG5, A1DZF0 |
| FNLAGNHEQEFLR (SEQ ID NO: 201) | 10 | Q5I6T2, B5TYU1, Q9FZ11, Q8LL03, Q9SQH7, Q647H4, Q6T2T4, Q8LKN1, Q647H3, A1DZF0 |
| NALFVPHYNTNAHSIIYALR (SEQ ID NO: 202) | 9 | Q5I6T2 (3x), B5TYU1 (3x), Q9FZ11 (3x), Q9SQH7 (3x), Q647H4 (3x), Q6T2T4 (3x), Q8LKN1 (3x), Q647H3 (3x), A1DZF0 (3x) |
| SPDIYNPQAGSLK (SEQ ID NO: 203) | 9 | Q5I6T2, B5TYU1, Q9FZ11, O82580, Q647H4, Q6T2T4, Q8LKN1, Q647H3, A1DZF0 |
| WLGLSAEYGNLYR (SEQ ID NO: 204) | 9 | Q5I6T2, B5TYU1, Q9FZ11, Q9SQH7, Q647H4, Q6T2T4, Q8LKN1, Q647H3, A1DZF0 |
| VYDEELQEGHVLVVPQNFAVAGK (SEQ ID NO: 205) | 7 | Q5I6T2, B5TYU1, Q9FZ11, O82580, Q9SQH7, Q647H3, A1DZF0 |
| SQSENFEYVAFK (SEQ ID NO: 206) | 6 | O82580 (3x), Q9SQH7 (3x), Q647H4 (3x), Q6T2T4 (3x), Q8LKN1 (3x), A1DZF0 (3x) |
| AGQEQENEGGNIFSGFTPEFLAQAFQVDDR (SEQ ID NO: 207) | 4 | Q647H4 (3x), Q6T2T4 (3x), Q8LKN1 (3x), Q647H3 (3x) |
| GENESDEQGAIVTVR (SEQ ID NO: 208) | 4 | Q647H4, Q6T2T4, Q8LKN1, Q647H3 |
| QQYERPDEEEEYDEDEYEYDEEER (SEQ ID NO: 209) | 4 | Q647H4, Q6T2T4, Q8LKN1, Q647H3 |
| SQSDNFEYVAFK (SEQ ID NO: 210) | 4 | Q5I6T2, B5TYU1, Q9FZ11, Q647H3 |
| TANDLNLLILR (SEQ ID NO: 211) | 4 | Q5I6T2, Q9FZ11, O82580, Q8LKN1 |
| TANELNLLILR (SEQ ID NO: 212) | 4 | B5TYU1 (3x), Q647H4 (3x), Q6T2T4 (3x), A1DZF0 (3x) |
| TDSRPSIANLAGENSFIDNLPEEVVANSYGLPR (SEQ ID NO: 213) | 4 | Q647H4 (3x), Q6T2T4 (3x), Q8LKN1 (3x), A1DZF0 (3x) |
| AHVQVVDSNGDR (SEQ ID NO: 214) | 3 | Q647H4, Q6T2T4, Q8LKN1 |

TABLE 22-continued

Ara h3 Sequences Identified in Prepared Peanut Extract

| Ara h3 Peptide Sequence | # Appearance in 16 UniProt References | UniProt Reference Nos |
|---|---|---|
| AQSENYEYLAFK (SEQ ID NO: 215) | 3 | Q0GM57, E5G077, Q6IWG5 |
| FNEGDLIAVPTGVAFWLYNDHDTD VVAVSLTDTNNNDNQLDQFPR (SEQ ID NO: 216) | 3 | B5TYU1, Q9SQH7, A1DZF0 |
| GADEEEEYDEDEYEYDEEDR (SEQ ID NO: 217) | 3 | Q5I6T2, B5TYU1, Q9FZ11 |
| SSNPDIYNPQAGSLR (SEQ ID NO: 218) | 3 | Q0GM57, E5G077, Q6IWG5 |
| SVNELDLPILGWLGLSAQHGTIYR (SEQ ID NO: 219) | 3 | Q0GM57, E5G077, Q6IWG5 |
| VFDEELQEGHVLVVPQNFAVAGK (SEQ ID NO: 220) | 3 | Q647H4, Q6T2T4, Q8LKN1 |
| VYDEELQEGHVLVVPQNFAVAAK (SEQ ID NO: 221) | 3 | Q0GM57, E5G077, Q6IWG5 |
| AGQEEENEGGNIFSGFTPEFLAQA FQVDDR (SEQ ID NO: 222) | 2 | B5TYU1, Q9FZ11 |
| AGQEEENEGGNIFSGFTPEFLEQA FQVDDR (SEQ ID NO: 223) | 2 | Q5I6T2, O82580 |
| FFVPPFQQSPR (SEQ ID NO: 224) | 2 | Q9SQH7, A1DZF0 |
| TDSRPSIANLAGENSIIDNLPEEV VANSYR (SEQ ID NO: 225) | 2 | Q0GM57 (3x), Q6IWG5 (3x) |
| AGQEEEDEGGNIFSGFTPEFLEQA FQVDDR (SEQ ID NO: 226) | 1 | Q9SQH7 |
| AGQEQENEGGNIFSGFTSEFLAQA FQVDDR (SEQ ID NO: 227) | 1 | A1DZF0 |
| GENESEEEGAIVTVK (SEQ ID NO: 228) | 1 | Q9FZ11 |
| GENESEEQGAIVTVK (SEQ ID NO: 229) | 1 | A1DZF0 (3x) |
| SPDEEEEYDEDEYAEEER (SEQ ID NO: 230) | 1 | A1DZF0 |
| SQSEHFLYVAFK (SEQ ID NO: 231) | 1 | Q647H2 |
| TDSRPSIANLAGENSIIDNLPEEV VANSYGLPR (SEQ ID NO: 232) | 1 | Q647H3 (3x) |
| TDSRPSIANLAGENSVIDNLPEEV VANSYGLPR (SEQ ID NO: 233) | 1 | B5TYU1 |
| TDSRPSIANQAGENSIIDNLPEEV VANSYR (SEQ ID NO: 234) | 1 | E5G077 |
| VFDEELQEGQSLVVPQNFAVAAK (SEQ ID NO: 235) | 1 | Q647H2 |

TABLE 23

Ara h6 Sequences Identified in Prepared Peanut Extract

| Ara h6 Peptide Sequence | # Appearance in 2 UniProt References | UniProt Reference Nos |
|---|---|---|
| IMGEQEQYDSYDIR (SEQ ID NO: 236) | 2 | Q647G9, A1DZE9 |
| QMVQQFK (SEQ ID NO: 237) | 1 | Q647G9 |

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

---

What is claimed:

1. A method for quantifying one or more peanut protein allergens in a composition, the method comprising:
   contacting a composition comprising one or more peanut protein allergens with an aqueous extract medium to produce an aqueous peanut extract;
   digesting the one or more peanut protein allergens present in the aqueous peanut extract to generate one or more peanut protein allergen digest products;
   fragmenting the one or more peanut protein allergen digest products to generate peptide fragments;
   analyzing the peptide fragments and/or the one or more peanut protein allergen digest products using a mass spectroscopic method to generate a peanut allergen signature; and
   determining an amount of the one or more peanut protein allergens in the composition by comparing the peanut allergen signature to a calibration curve,
   wherein the peanut allergen signature comprises allergen digest products from Ara h1, Ara h2, Ara h3 and Ara h6, and
   wherein the one or more peanut protein allergens in the aqueous peanut extract is present at a concentration of less than about 2 μg/ml.

2. The method of claim 1, wherein the mass spectroscopic method is selected from the group consisting of one or any combination of LC-MS, LC-MS-MS, nano-LC-MS-MS, and nanoHPLC-MS-MS.

3. The method of claim 1, wherein the one or more peanut protein allergen digest products are between about 4 amino acids and about 50 amino acids in length.

4. The method of claim 1, wherein the peanut allergen signature comprises Ara h1 allergen digest products having an amino acid sequence selected from the group consisting of SEQ ID NO: 17, SEQ ID NO:70, SEQ ID NO: 177, SEQ ID NO: 155, SEQ ID NO:93 and SEQ ID NO:40.

5. The method of claim 1, wherein the one or more peanut protein allergen digest products comprise all isoforms of Ara h1.

6. The method of claim 1, wherein the one or more peanut protein allergens are digested with one or more proteases selected from the group consisting of trypsin, endoproteinase Lys-C and endoproteinase Arg-C.

7. The method of claim 1, wherein the composition comprising one or more peanut protein allergens comprises an internal standard that comprises one or more heavy isotopes.

8. The method of claim 1, wherein the aqueous peanut extract is made from peanut flour, roasted peanuts or raw peanuts.

9. The method of claim 1, wherein the one or more peanut protein allergens in the aqueous peanut extract is present at a concentration of less than about 1.0 µg/ml.

10. The method of claim 1, wherein the one or more peanut protein allergens in the aqueous peanut extract is present at a concentration of less than about 0.5 µg/ml.

11. The method of claim 10, wherein the peanut allergen signature comprises allergen digest products from Ara h1, Ara h2, Ara h3 and Ara h6 having amino acid sequences selected from the group consisting of SEQ ID NO: 17, SEQ ID NO:70, SEQ ID NO:177, SEQ ID NO:197, SEQ ID NO: 198, SEQ ID NO: 199, SEQ ID NO:200, SEQ ID NO:201, SEQ ID NO: 236 and SEQ ID NO:237.

12. The method of claim 1, wherein the peanut allergen signature comprises allergen digest products that are present in a majority of isoforms of Ara h1, Ara h2, Ara h3 and Ara h6.

13. The method of claim 1, wherein the peanut allergen signature comprises digest products that do not contain missed proteolytic cleavage sites.

14. The method of claim 1, wherein the one or more peanut protein allergen digest products are between about 6 amino acids and about 30 amino acids in length.

15. The method of claim 1, wherein the one or more peanut protein allergen digest products are between about 15 amino acids and about 20 amino acids in length.

16. A method for quantifying one or more peanut protein allergens in a composition, the method comprising:
contacting a composition comprising one or more peanut protein allergens with an aqueous extract medium to produce an aqueous peanut extract;
digesting the one or more peanut protein allergens present in the aqueous peanut extract to generate one or more peanut protein allergen digest products;
fragmenting the one or more peanut protein allergen digest products to generate peptide fragments;
analyzing the peptide fragments and/or the one or more peanut protein allergen digest products using a mass spectroscopic method to generate a peanut allergen signature comprising allergen digest products from Ara h1, Ara h2, Ara h3 and Ara h6; and
determining an amount of the one or more peanut protein allergens in the composition by comparing the peanut allergen signature to a calibration curve,
wherein the one or more peanut protein allergens in the aqueous peanut extract is present at a concentration of less than about 1.5 µg/ml.

* * * * *